United States Patent [19]

Alexander et al.

[11] 4,306,027
[45] * Dec. 15, 1981

[54] PESTICIDALLY RESISTANT RHIZOBIUM AND AGRONOMIC USE THEREOF

[75] Inventors: Martin Alexander; Oluwasuyi Odeyemi, both of Ithaca, N.Y.

[73] Assignee: Cornell Research Foundation, Inc., Ithaca, N.Y.

[*] Notice: The portion of the term of this patent subsequent to Jun. 13, 1995, has been disclaimed.

[21] Appl. No.: 893,116

[22] Filed: Apr. 4, 1978

Related U.S. Application Data

[62] Division of Ser. No. 722,318, Sep. 10, 1976, Pat. No. 4,094,097.

[51] Int. Cl.$^3$ .......................... C12N 1/20; C12R 1/41
[52] U.S. Cl. ..................................... 435/253; 435/878
[58] Field of Search ............... 435/168, 172, 245, 253, 435/878; 47/1, 58, 57.6

[56] References Cited

U.S. PATENT DOCUMENTS

| | | | |
|---|---|---|---|
| 3,168,796 | 2/1965 | Scott et al. | 47/1 |
| 3,616,236 | 10/1971 | Delin | 435/ |
| 4,094,097 | 6/1978 | Alexander et al. | 435/ |

OTHER PUBLICATIONS

Biswas, et al., "Nodulation of *Trifolium alexandrium* by Penicillin Treated *Rhizobium trifolli*", Chem. Absts., vol. 82, No. 5, pp. 418 (1975), Abs. No. 30192z.

Namdeo, et al., "Herbicidal influence on Growth Sensitivity and Mutation Transformation in Rizobia", Chem. Absts., vol. 80, No. 1, p. 235 (1974), Abs. No. 26126.

Sud, et al., "Growth Promoting Effect of TCA and Dalapon on Rhizobium Strains", Chem. Absts., vol. 79, No. 9, p. 284 (1973), Abs. No. 52297c.

Kecskes, et al., "Effect of Some Fungicides on *Rhizobium leguminosarum* species", Chem. Absts., vol. 79, No. 25, p. 70, (1973), Abs. No. 143388z.

Elek, et al., "Effect of Some Seed Treatments Using Microelements and Fungicides on Vetch Plants Grown From Seeds Inoculated with Rhizobia", Chem. Absts., vol. 79, No. 13, p. 123 (1973), Abs. No. 745601c.

Kecskes, et al., "Compatability of Fungicide Treatment and Rhizobium Inoculation of Vetch Seed", Chem. Absts., vol. 79, No. 8, p. 125 (1973), Abs. No. 101547v.

Vincent, "A Manual for the Practical Study of Root-Nodule Bacteria", IBP Handbook No. 15, Blackwell Scientific Publication, Oxford (1970).

*Primary Examiner*—Thomas G. Wiseman
*Attorney, Agent, or Firm*—Jones, Tullar & Cooper

[57] ABSTRACT

This invention relates to Rhizobium strains having good infecting and nitrogen-fixing characteristics and which are resistant to fungicides. These strains are produced by cultivating a Rhizobium strain sensitive to a particular fungicide in the presence of an amount of the fungicide, and for a time less than that sufficient to kill the entire Rhizobium population but sufficient to kill a majority of the population. The remaining Rhizobium population is isolated and recultured in the presence of an increased amount of the fungicide, again an amount and a time less than sufficient to kill the entire Rhizobium population, but sufficient to kill a majority of the population. This procedure is repeated for sufficient passages, with increasing amounts of said fungicide, to provide a Rhizobium strain sufficiently resistant to said fungicide so that the Rhizobium strain multiplies and enters into a nitrogen-fixing symbiosis in the presence of agriculturally effective amounts of the fungicide.

1 Claim, 6 Drawing Figures

PESTICIDALLY RESISTANT RHIZOBIUM AND AGRONOMIC USE THEREOF

This is a division of application Ser. No. 722,318, filed Sep. 10, 1976. U.S. Pat. No. 4,094,097.

STATE OF THE ART

The importance in the humid tropics of nitrogen fixed symbiotically by Rhizobium in association with legume species is extremely great, as farmers still rely largely upon shifting cultivation as a major means of restoring and sustaining soil fertility and world fertilizer usage is small.

Even where fertilizers are available, a substantial proportion of N applied to soils is often unavailable to crops because of denitrification and leaching losses; these processes may even give rise to potential secondary problems of air and water pollution. Besides, the energy-consuming, relatively inefficient chemical fixation of N by the Haber-Bosch process contributes only $2.2 \times 10^{10}$ kg/yr N to the global fixed N pool compared to $9.1 \times 10^{10}$ kg/yr provided by the more efficient, natural, biological N fixation (Hardy et al, "The Biochemistry of Nitrogen Fixation", *Adv. Chem. Series* No. 100:219-247, 1971). It is in view of these fertilizer problems that many developing countries are currently considering the Rhizobium-legume symbiosis as a means of increasing crop yields and providing adequate plant proten without the input of costly and often unavailable fertilizer N.

This interest in symbiotic N fixation had led biochemists, chemist and microbial ecologists to discover that their knowledge of the ecology of Rhizobium is scanty (Alexander, "Ecology of Nitrogen-Fixing Organisms". Paper presented at a symposium on biological nitrogen fixation in farming systems of humid tropics at Int. Inst. Tropical Agric., Ibadan, Nigeria, Oct. 1975.)

Of considerable importance to the survival and infectivity of rhizobia in soils are several abiotic factors, and there is a body of literature on the various environmental factors that influence the survival of root-nodule bacteria in soils. Some of the more important factors are soil moisture, alkalinity and acidity, temperature, aeration and the presence of toxic chemicals. Reviews on these factors have been written by Fred et al., "Root Nodule Bacteria and Leguminous Plants", University of Wisconsin Press, Madison, Wis., (1933); van Schreven, "Some Factors Affecting the Uptake of Nitrogen by Legumes" in "Nutrition of Legumes", Hallsworth (ed.), Butterworths, London, 137-163 (1968); Vincent, "Environmental Factors in the Fixation of Nitrogen and Legumes", in "Soil Nitrogen", Bartholomew et al. (ed.) p. 385-435, *Am. Soc. Agron.*, Madison, Wis. (1965), and most recently by Lie, "Environmental Effects on Nodulation and Symbiotic Nitrogen Fixation", in "The Biology of Nitrogen Fixation", Quispel (ed.), North-Holland Publishing Co., Amsterdam, 555-582 (1974). Only one of these reviewers wrote of the effect of toxic chemicals on the survival of rhizobia in soils and this portion of his test was quite short.

Pesticides may exhibit directly toxicity to the various strains of Rhizobium and may affect the nodulation process itself via either their effects on the host plant on their influence on th process of infection by the bacterium.

Several insecticides are known to exercise adverse effects on rhizobia and the nodulation process. For instance, depressed nodulation has been reported for 1,1,1-trichloro-2,2-bis(p-chlorophenyl) ethane (DDT) on clover and soybean, and for 1,2,3,4,5,6-hexachlorocyclohexane (BHC) on clover. Reduced or depressed nodulation of alfalfa, peas, and vetches as a result of prior treatment of the seeds with the insecticide, O,O-dimethyl S-(N-methacetamide) phosphorodithioate (rogor) have been demonstrated. Similarly, by means of a pot experiment, it has been shown that application of 10 to 50 ppm of 1,4,5,6,7,8,8-heptachloro-3a,4,7,7a-tetrahydro-4,7-methanoindene (heptachlor), 2-methyl-2-(methylthio)propionaldehyde O-(methylcarbamoyl) oxime (temik), DDT or BHC considerably decreased the numbers of nodules formed on clover and broad bean roots. Relatively low concentrations of 1,2,3,4,10,10-hexachloro-1,4,4a,5,8,8a-hexahydro-endo-1,4-exo-5,8-dimethanonaphthalene (aldrin) and 1,1-ethylene-2,2-bipyridylium dibromide (diquat) have been found to be incompatible with nodulation of alfalfa and red clover. However, Rhizobium strains vary widely in their susceptibility to insecticides, and some of them are relatively tolerant to the concentrations of insecticidal chemicals used in the field.

It is known in the art that some of the substituted phenols such as 2,3,4,5,6-pentachlorophenol (PCP), 2-methyl-4,6-dinitrophenol (DNOC), and isopropyl carbanilate (propham), which are used as herbicides, have been found to suppress populations of free-living, nitrogen-fixing strains of Azotobacter and Clostridium as well as those of root-nodule bacteria at rates not much above those used in the fields. The pesticides 2-chloro-4,6-bis(ethylamino)-s-triazine (Simazine), and 2-chloro-4-ethylamino-6-isopropylamino-s-triazine (Atrazine) can also suppress numbers of Azotobacter when applied as herbicides in maize fields. The phenoxy herbicides can be inhibitory at field rates, depending on the species, with the nodulation process itself being more sensitive than the growth of the rhizobia. In general, fast-growing strains of rhizobia seem to be more tolerant to herbicides than their slow-growing counterparts, Kaszubiak, *Acta. Microbiol. Pol.* 15:357-364 (1966). For instance, the slow-growing *Rhizobium meliloti* seems to be more susceptible to herbicides than *Rhizobium trifolii* and *Rhizobium leguminosarum* (Jensen, *Tidsskr Planteaul.* 73:309-317 1969).

It has been estimated that about 80% of all legume diseases are fungal in origin. Unless all these diseases are controlled chemically or otherwise, a drastic reduction in crop yields would be inevitable.

It is also known that as much as an 80% increase in yield of legumes can be attained by the use of antifungal plant and seen protectants.

However, it is also equally well known now that the viability of rhizobia in soils is often adversely affected by the usual doses of pesticides, particularly fungicides, applied to soils or seeds, often giving rise to a substantial decrease in yields. For instance, the U.S. Environmental Protection Agency (EPA) recommended rates of 2,3,5,6-tetrachloro-1,4-benzoquinone (spergon) application to alfalfa, 7.4 oz/100 lb. of seeds would be lethal to most rhizobia. This problem is sometimes aggravated by the fact that many fungi acquire resistance to some fungicides, necessitating the use of an unusually high dosage of seed protectants by farmers in order to control some of the fungal diseases of legumes. Resistance of a disease-causing fungus to a fungicide can create a practical problem especially when the margin between fungitoxic and phytotoxic concentrations of the antifungal agent is small. Both the macro- and the microsymbionts as well as the nodulation process could be adversely affected by some of the more toxic pesticides.

Curley and Burton, *Agron. J.* 67:807-808 (1975), found that 83% of the *Rhizobium japonicum* cells applied to PCNB-treated soybean seeds were killed by the fungicide 4 hours after rhizobial inoculation; by comparison, a 20% kill by 5,6-dihydro-2-methyl-1,4-oxathiin-3-carboxanilide (carboxin) or captan, and 6% loss in viable count of the bacteria on inoculated control seeds during the same time period was noted. According to Curley and Burton, PCNB treatment also greatly reduced the nodulation of soybean tap roots. Several strains of *R. meliloti, R. leguminosarum,* and *R. trifolii* were inhibited by low concentrations of captan and dimethyldithiocarbamate, Gillberg, *Arch. Mikrobiol.* 75:203-208 (1971). Kecskes and Vincent, *Agrokem. Talait.* 18:57-70 (1969), Petrovic, *Mikrobiologia.* 7:183-193 (1970), and Wrobel (1963) found that mercury-containing fungicides, especially N-cyano-N'-(methylmercury) guanidine (panogen) and ceresan, were highly toxic to several strains of Rhizobium and adversely affected legume nodulation.

In field tests, Kecskes, in "Colloque International, Action des Pesticides et Herbicides sur la Microflore et la Faunule du sol Biodegradation Tellurique de leurs Molecules" Ponchon & Voets (ed.), Rijksuniversiteit, Gent. p. 205-514 (1970), found that spergon and cuprous oxide (cuprox) delayed nodulation and significantly decreased the yield of vetch. Golebiowska, *Pam. Pulawski* 18:368 (1965) also reported delayed nodulation and decreased yields in legume seeds treated with antifungal seed dressings. Even tetramethylthiram disulfide (thiram), which has been claimed by some authors to be reasonably non-inhibitory to rhizobia and non-phytotoxic, was found to inhibit the growth of *R. leguminosarum* on pea seeds when used at recommended rates (Sidhu and Kahlon, *Hindustan Antibiot. Bull.* 14:71-74, (1971). Brakel, *Ann. Inst. Pastuer* 105:143-149 (1963) and Golebiowska, *Pam. Pulawski* 18:368 (1965) have also shown thiram to be highly toxic to many strains of Rhizobium, especially those nodulating species of Trifolium, Phaseolus, and Pisum.

The bulk of the work done in the area of pesticide-rhizobia interaction has been concerned mainly with the screening of different strains of rhizobia for their compatibility with the various types of pesticides (Brakel, supra; Goss and Shipton, *J. Agric. West. Aust.* 6:659-661 (1965); Kaszubiak, loc. cit.; Mikhailova, *Khim. sel'sk Khoz.* 204-206 (1968); Jensen, loc. cit.; Audus (see Kecskes, supra, p. 465-492) (1970); Sud and Gupta, *Arch. Mikrobiol* 85:19-22 (1972); Kapusta and Rowenhorst, *Agron. J.* 65:112-115 (1973); Kecskes and Vincent, *Acta Agron. Acad. Sci. Hung.* 22:249-263 (1973); Curley and Burton, loc. cit. Most of these authors found that most of the pesticides tested were inhibitory to rhizobia.

One approach to the problem is to prevent an effect on the root-nodule bacteria by the pesticidal action of fungicides, herbicides, insecticides, and nematicides. Diatloff, *J. Aust. Inst. Agric. Sci.* 36:293-294 (1970), attempted to solve this problem by coating fungicide-dusted clover seeds with a layer of polyvinyl acetate resin before inoculating with rhizobia to separate bacteria from the seed dressing. Klintsare, *Trudy Inst. Mikrobiol. Akad. Nauk. Latv. SSR.* 14:39-48 (1961), suggested that seeds be treated with fungicides 10 days before planting to prevent detrimental effects of fungicides on rhizobia.

Some authors have suggested that special methods of applying pesticides might prevent their antirhizobial effects. For instance, Mackenzie et al., *Aust. J. Exp. Agric. Anim. Husb.* 12:428-432 (1972), reported that, in field experiments, application of p-dimethylaminobenzenediazo sodium sulfonate (dexon) and 1,4-dichloro-2,5-dimethoxybenzene (demosan) by banding the fungicides with seeds prevented the damping-off caused by *Pythium irregulare* and increased the establishment of alfalfa without adversely affecting nodulation. However, in the same experiment, they found that the band application of captan and PCNB reduced nodulation. Desai and Bucholtz, *Iowa State J. Sci.* 37:79-85 (1962), also reported that pelleting alfalfa seeds with thiram gave better yields than slurrying or dry-dust application of the seed protectant. In U.S. Pat. No. 3,616,236, to Delin, there is described the production of Rhizobium strains having good infecting and nitrogen-fixing characteristics by cultivating the strain, the subjecting it to drying whereby those strains which are sensitive to drying are destroyed and those strains which are resistant to drying survive. The surviving strains are then cultivated and subjected to at least one more drying treatment.

DESCRIPTION OF THE INVENTION

This invention relates to Rhizobium strains having good infecting and nitrogen-fixing characteristics and which are resistant to fungicides. These strains are produced by cultivating a Rhizobium strain sensitive to a particular fungicide in the presence of an amount of the fungicide, and for a time less than that sufficient to kill the entire Rhizobium population, but sufficient to kill a majority of the population. The remaining Rhizobium population is isolated and recultured in the presence of an increased amount of the fungicide, again an amount and a time less than sufficient to kill the entire Rhizobium population, but sufficient to kill a majority of the population. This procedure is repeated for sufficient passages, with increasing amounts of said fungicide, to provide a Rhizobium strain sufficiently resistant to said fungicide so that the Rhizobium strain multiplex and enters into a nitrogen-fixing symbiosis in the presence of agriculturally effective amounts of the fungicide.

It is known that all Rhizobium strains do not enter into nitrogen-fixing symbiosis with all leguminous plants, but that the nitrogen-fixing ability is dependent both on the plant in question and the bacteria. Thus the fungicide sensitive strain to be treated should be Rhizobium strain known to enter into a nitrogen-fixing symbiosis with the particular legumes intended to be grown in the presence of the fungicide resistant strain provided by the procedures of this invention.

Specifically, the following fungicide sensitive Rhizobium strains can be cultivated by the methods of this invention to provide pesticide resistant strains useful with the following legumes:

R. *leguminosarum*—peas
R. *trisofii*—clover
R. *phaseoli*—common beans
R. *japonicum*—soybeans
R. *lupini*—lupines
R. *meliloti*—alfalfa
Cowpea Rhizobia—cowpeas, peanuts, etc.

The method of the present invention is essentially characterized in that a normal wild or parent fungicide sensitive Rhizobium culture, that is a culture destroyed or inhibited by the presence of an agriculturally significant amount of that particular fungicide, that is a conventional amount useful to provide the desired fungicidal activity, is cultivated on a Rhizobium substrate in a manner known per se, except that a critical amount of the fungicide, as described above, is introduced into the culture so as to allow for survival of bacteria. The survivors are then recultivated to allow the surviving bacteria to reproduce; the procedure can be repeated one or more time to produce a final product consisting of a Rhizobium strain that is resistant to the particular fungicide to a particular desired extent. Preferably at least 90 percent, and more preferably in excess of 99 percent, of the bacteria are killed in the course of each of the culturing steps wherein the fungicide has been introduced.

As to the basic procedure manipulative techniques, including culture materials, test procedures, bacteria storage and seen innoculation techniques, attention is directed to J. M. Vincent, "A Manual for the Practical Study of Root-Nodule Bacteria", IBP Handbook, No. 15, Blackwell Scientific Publication, Oxford, 1970 (hereinafter referred to as Vincent (1970)). The material contained therein is considered within the skill of the art, thus many of these procedures are not discussed or described in detail. For example, Vincent (1970) describes the routine complex media for Rhizobium culture as a yeast extract manitol broth, and also describes other media which are useful.

In the process of the invention, the parent Rhizobium is cultured in a conventional manner with the exception that there is added to the medium an amount of the fungicide as set forth above. The fungicide is usually added to the medium prior to or at the time the Rhizobium is added, although the fungicide can be added later after growth has begun. In each instance of addition, the amount of fungicide to be added can be most readily determined by a screening series of cultures containing varying amounts of fungicide, selecting from the series, for subsequent passage or culture and recovery, that culture which displays the desired amount of remaining viable Rhizobium.

The passage and recovery techniques employed are those conventionally employed in the art. Typically, where only a small number of rhizobia survive each passage, i.e. were will in excess of 99% of the rhizobia population are killed in each passage with increasing amounts of fungicide, between about 60 to 12 passages are required to obtain rhizobia which is resistant to conventional agriculturally applied amounts of the fungicide.

The fungicide resistant strains of the invention have the same identification characteristics as the original pesticide sensitive strain except they are significantly more tolerant to the particular fungicide. Thus, their identification is readily possible by comparison with characteristics of the known sensitive strain.

The fungicide resistant Rhizobium strains can be inoculated into compatible leguminous seeds in any manner known in the art as useful for so applying Rhizobium; for example, see Vincent (1970), chapter 6, The Production, Control and Use of Legume Inoculants. The minimum number of rhizobia applied to the seed cay vary from a few to many thousands according to the conditions encountered before and after sowing. Usually it is desirable that the applied number of rhizobia per seed be at least about 100. The fungicide resistant Rhizobium strains are especially useful for inoculating leguminous seeds which are also treated with the fungicide to which the rhizobia has specifically enhanced resistance.

Further, the use of fungicide resistant Rhizobium allows for bacterial control, in that application of the fungicide can be used to kill or retard sensitive bacteria without adverse effect on the fungicide resistant Rhizobium.

The fungicides which can be employed in the process of this invention include all the agriculturally useful legume seed or soil fungicides which adversely affect rhizobia; especially useful are the carbamic acid derivatives, including thiocarbamates, including dithiocarbamates, dimethyldithiocarbamates, thiruam disulfides, especially thiram; as well as halogenated organic compounds, including the benzoquinones and napthoquinones.

Figure 1:
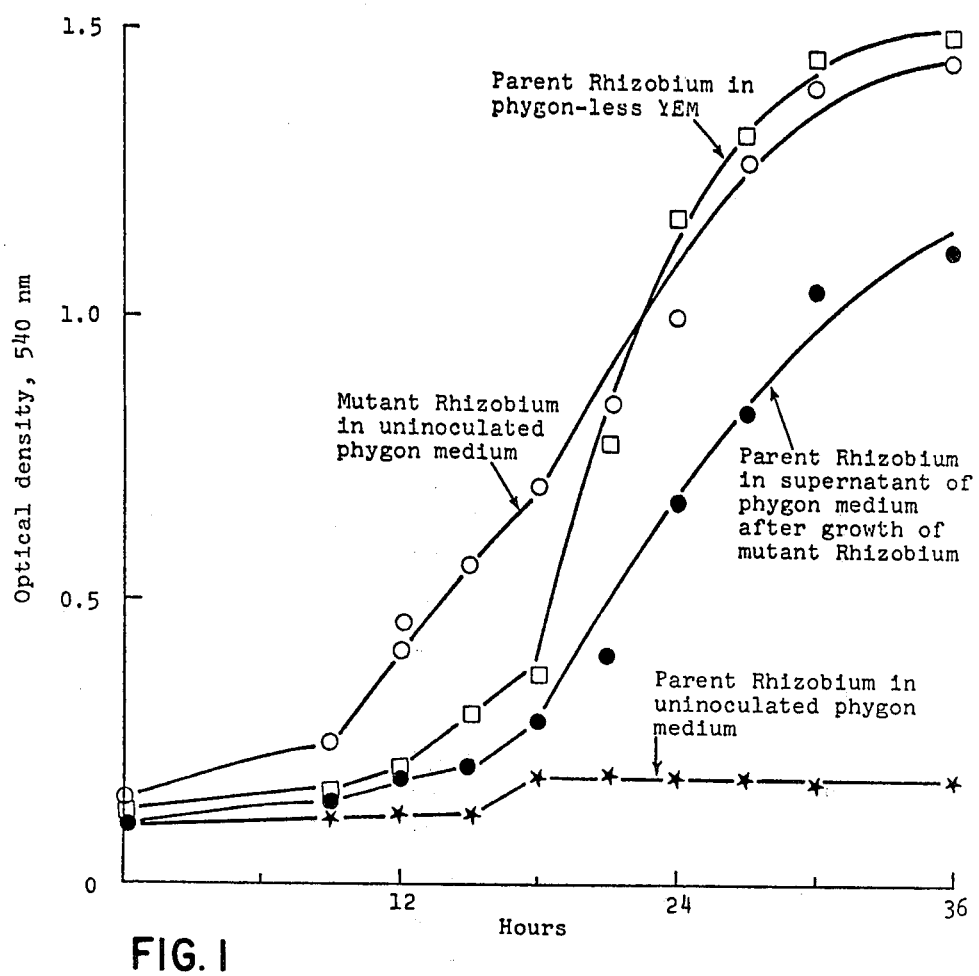
FIG. 1 shows the growth of phygon-sensitive and resistant cowpea Rhizobium in YEM amended with the supernatant fluid derived from YEM initially containing 400 ppm phygon incubated with or without mutant cowpea Rhizobium for five days. (See Example 9)

Illustrating the invention are the following examples, which are not to be construed as limiting the invention to their details. All parts and percentages in the examples, as well as throughout specification, are by weight unless otherwise specified. All temperatures are degrees Centigrade, unless otherwise specified.

There follow several examples describing the processes and products of the invention, together with their utility and an investigation of the causes of the results achieved. In these examples, unless otherwise stated, the following are considered as standards:

Cultures. The Rhizobium strain K04SR was obtained from Dr. S. O. Keya, Cornell University, Ithaca, N.Y. It was originally isolated by Dr. Keya from nodules of a cowpea plant (*Vigna unguiculata*) growing at an experimental plot in Makerere, Uganda. *Rhizobium meliloti* 87 and *Rhizobium phaseoli* 203 came from the culture collection of the Laboratory of Soil Microbiology, Cornell University, Ithaca, N.Y. All the cultures were treated for infectivity and effectiveness using the procedure of Vicent, "A Manual for the Practical Study of Root-Nodule Bacteria", Blackwell Scientific Publications, Oxford, (1970).

Culture media. Media for culture of rhizobia consisted of (g/l): $K_2HPO_4$, 1.0; $KH_2PO_4$, 1.0; NaCl, 0.20; $MgSO_4$, 0.18; $CaSO_4.2H_2$, 0.13, $KNO_3$, 1.0; $FeCl_3.4H_2O$, 0.08; yeast extract, 1.0; mannitol, 10.0; agar (where a solid medium was desired), 15.0; and distilled water, 1 liter. The final pH of this yeast extract-mannitol (YEM) medium was adjusted to 7.0

Maintenance of cultures. Stock cultures of rhizobia were maintained on YEM agar slants and stored at 4° C. These cells were transferred to a fresh medium every 3 months. Fungicide-resistant variants of these rhizobia were maintained on YEM slants as well as on petri dishes containing YEM agar with or without fungicides and stored at 4° C. Subcultures were made every 6 weeks.

Purification of chemicals. The commercially available thiram (tetramethylthiram disulfide) and phygon (2,3-dichloro-1,4-naphthoquinone, sometimes called dichlone) were purified by recrystallization two times from hot ethanol. Technical grade spergon (2,3,4,6-tetrachloro-p-benzoquinone, also called chloranil) was purified by means of a specially devised procedure using column chromatography as follows. A solvent mixture of toluene-benzene-ethyl acetate-acetic acid (50:40:40:10) was passed through a 51×2 cm glass column filled with benzene-moistened 100-200 mesh silica gel, grade 923 (obtained from Schaar and Co., Chicago, Ill.). A solution of crude spergon in benzene was then passed through the column. As the spergon solution passed through the column the golden-yellow spergon moved through the solvent mixture in the column while a dark, bluish brown impurity remained at the top of the column. The spergon-containing eluate was collected in a round bottom Erlemeyer flask and subjected to flash evaporation. The spergon residues were then dissolved in and recrystallized from benzene. The purified spergon was subjected to a thin-layer chromatographic (TLC) analysis using two different solvent mixtures; toluene-benzene-ethyl acetate-acetic acid (50:40:40:10) and hexane-ethyl acetate-ethanol-acetic acid (90:70:40:10). Only one golden-yellow spot was observed on the TLC plates in each of four replications, as opposed to two spots obtained using the original, unpurified chemical.

Sterilization techniques. Stock solutions of thiram, spergon, and phygon were prepared by dissolving the required amount of each fungicide in acetone. The solutions were then sterilized by filtering them through 0.20 μm fluorocarbon Millipore filters (that are chemically stable to organic solvents and acids) into sterile bottles. The resulting solutions were stored at 4° C. for periods up to 4 weeks. All other media were sterilized by autoclaving for 15 mins. at 15 lbs pressure and 121° C.

Iroquois variety of alfalfa, long, tender green beans, and whipporwill variety of cowpea seeds of reasonably uniform sizes were surface-sterilized by rinsing them with 95% ethanol and later immersing them for 3 mins. in 0.2% $HgCl_2$ acidified with 5 ml of concentrated HCl/liter. The seeds were then washed thoroughly with six changes of sterile distilled water.

EXAMPLE 1

Isolation of Fungicide-Resistant Rhizobia

The medium used for the maintenance of cultures and for the isolation of fungicide-tolerant rhizobia was YEM. Fungicide-resistant strains of infective rhizobia were obtained by growing the cultures in 50 ml of YEM broth contained in 125-ml Erlenmeyer flasks. The broths were treated with 50 ppm of each fungicide and the flasks incubated on a rotary shaker at 30° C. for 5 days. The survivors of this concentration of fungicide were later transferred three times to another set of YEM media amended with 70 or 100 ppm of each fungicide and incubated on the same shaker (operating at 180 rpm) for 5 days. Cultures obtained from resistant cells of each strain were washed three times with 0.1 M phosphate buffer, pH 7.0, before being transferred to a fresh YEM broth containing a higher concentration of each fungicide than previously used. After seven successive transfers, isolates resistant to a considerably higher concentration of fungicide than the parent strain were obtained. Thus, by this sequential exposure of the test organism to higher and higher concentrations of the respective fungicides, strains of R. phaseoli 203, R. meliloti 87, and cowpea Rhizobium K04SR resistant to 250 ppm spergon, 300 ppm thiram, and 1,000 ppm phygon, respectively, were obtained. These adapted strains were grown in 50 ml of YEM broth containing the level of fungicide to which each was tolerant for another six successive transfers. In each instance, the 125-ml Erlenmeyer flasks containing the YEM media and the adapted strains of rhizobia were incubated on a rotary shaker at 30° C. for 5 days. The maximum inhibitory concentration of the fungicides was determined turbidmetrically by measuring growth of each parent or adapted Rhizobium in YEM broth containing different concentrations of each chemical. Measurement of optical density was performed with a spectrophotometer, model Spectronic 20, at a wavelength of 560 nm.

Growth of Fungicide-Resistant Strains of Rhizobium at Various Fungicide Concentrations.

Resistant and sensitive strains of R. meliloti 87TR, R. phaseoli 203CR, and cowpea Rhizobium K04SRPR were grown in side-armed Erlenmeyer flasks containing 50 ml of YEM broth amended with 0 to 400 ppm of thiram, spergon, and phygon, respectively. All flasks were incubated on a shaker at 30° C. The growth of each strain was determined by measuring optical density at 30 minute intervals for 39 hours using a spectrophotometer (model Spectronic 20) at 560 nm. The generation time of the fungicide-tolerant rhizobia and of their fungicide-sensitive parent strains in YEM media amended with different levels of the fungicides are shown in Table 1. The adapted strains were able to grow at considerably higher concentrations of the fungicides than their parent strains.

TABLE 1

| Generation Time of Fungicide-Sensitive or Resistant Strains of Rhizobium in YEM Media Containing Different Levels of Fungicides | | | |
|---|---|---|---|
| Fungicide | Conc. of Fungicide, ppm | Generation Time, Hr. | |
| | | Parent R. meliloti 87 | Adapted R. meliloti 87TR |
| Thiram | 0 | 3.0 | 3.0 |
| | 20 | 6.0 | 3.1 |
| | 50 | 7.8 | 6.0 |
| | 100 | ng* | 9.0 |
| | 200 | ng | 9.0 |
| | | Parent R. phaseoli 203 | Adapted R. phaseoli 203CR |
| Spergon | 0 | 3.6 | 4.2 |
| | 20 | 4.8 | 4.2 |
| | 50 | 10.8 | 4.2 |
| | 70 | ng | 4.2 |
| | 100 | ng | 6.0 |

TABLE 1-continued

Generation Time of Fungicide-Sensitive or Resistant Strains of Rhizobium in YEM Media Containing Different Levels of Fungicides

| Fungicide | Conc. of Fungicide, ppm | Generation Time, Hr. | |
|---|---|---|---|
| | | Parent cowpea Rhizobium K04SR | Adapted cowpea Rhizobium K04SRPR |
| | 150 | ng | 6.0 |
| Phygon | 0 | 3.0 | 3.1 |
| | 20 | 3.6 | 3.6 |
| | 50 | 6.6 | 4.0 |
| | 100 | ng | 5.6 |
| | 400 | ng | 6.6 |

*No growth.

EXAMPLE 2

Occurrence of Cross-Resistance

The following tests were conducted to find out whether acquired resistance of a Rhizobium strain to one chemical could result in resistance of the same strain to another chemical. Fifty milliliters of YEM broth was introduced into each of several 300-ml side-armed Erlenmeyer flasks and autoclaved for 15 min. at 121° C. Some of the media were later treated with 50 ppm of each fungicide, and others amended with 70 ppm of each chemical. One milliliter of a washed suspension of a 3-day old *R. phaseoli* (optical density 0.10 at 550 nm) that was resistant to spergon was introduced into a broth containing 50 or 70 ppm of phygon, and another 1.0 ml used to inoculate another broth amended with 50 or 70 ppm of thiram. Similarly, cells of thiram-tolerant *R. meliloti* were used to inoculate spergon-or phygon-containing YEM media and cells of phygon-resistant cowpea Rhizobium were used to inoculate YEM broth treated with thiram or spergon. That is, cells of a Rhizobium strain that was resistant to a particular fungicide were used to inoculate YEM media containing fungicides to which other adapted strains of rhizobia were resistant. The side-armed flasks containing the inoculated media were then incubated on a 180 rpm speed rotary shaker for 5 days at 30° C. Each flask was examined for bacterial growth on each of the 5 days. Turbidimetric measurement of growth was performed with a spectrophotometer, model Spectronic 20, at a wavelength of 560 nm. In this way, each of the fungicide-resistant strains was tested for resistance to each of the other fungicides. There was no growth of bacteria in any of the flasks. It was therefore concluded that none of the fungicide-tolerant strains exhibited cross-resistance to any of the other antifungal chemicals.

EXAMPLE 3

One milliliter of a washed cell suspension of each of the adapted strains of rhizobia was introduced into 50 ml of YEM prepared in 125-ml Erlenmeyer flask. The flasks were then incubated on a rotary shaker (operating at 180 rpm) for 3 days at 30° C. On the third day, each culture was washed 3 times with 0.1 M phosphate buffer (pH 7.0) and 1.0 ml of this washed cell suspension was transferred to another 50 ml of YEM medium contained in a 15-ml flask, which was again incubated under the conditions described above. In this way, six serial subcultures of the fungicide-tolerant strains of rhizobia were grown in fungicide-free YEM media. Immediately after washing the cells of the sixth serial subculture, approximately $10^4$ cells/ml of each strain was introduced into 50 ml of YEM broth prepared in 125-ml Erlenmeyer flask which had been treated with a concentration of the fungicide inhibitory to the wild-type strain. Another 50 ml of medium which was fungicide-free was also inoculated with about $10^4$ cells/ml of the same strain of Rhizobium. In this way, approximately $10^4$ cells/ml of *R. meliloti*, *R. phaseoli* and cowpea Rhizobium, which had been grown for six successive times in fungicide-free media, were transferred immediately to YEM media with or without 150 ppm thiram, 100 ppm spergon, and 200 ppm phygon, respectively. Each set of experiments was in triplicate, and each flask was incubated on a 180 rpm speed rotary shaker for 3 days at 30° C. On the third day of incubation, a 1.0 ml sample was taken from each flask and subjected to a serial dilution and plate counting. The results are shown in Table 2.

TABLE 2

The Relative Numbers of Each Adapted Strain of Rhizobium in YEM with or without Fungicide, as a Means of Assessing the Stability of Fungicide-Resistant Trait[a]

| Strain of Rhizobium | No. of rhizobia/ml in | |
|---|---|---|
| | YEM alone | YEM + fungicide[b] |
| *R. meliloti* 87TR | $4.4 \times 10^7$ | $3.9 \times 10^7$ |
| *R. phaseoli* 203CR | $8.6 \times 10^6$ | $1.2 \times 10^7$ |
| Cowpea Rhizobium K04SRPR | $6.3 \times 10^7$ | $2.9 \times 10^7$ |

[a]YEM broth inoculated with about $10^4$ rhizobial/ml.
[b]YEM amended with 150, 100, and 200 ppm of thiram, spergon, and phygon, respectively.

EXAMPLE 4

Nodulation Ability of Fungicide-Resistant Rhizobia

In order to determine if the fungicide-resistant strains of rhizobia still retained their ability to effect legume root-nodule formation in spite of their newly acquired characteristics of toxin-resistance, the adapted strains of rhizobia were subjected to a laboratory nodulation test using a seedling agar-tube method as described by Vincent (supra). *R. meliloti* 87TR (a thiram-tolerant stain), *R. phaseoli* 203CR (a spergon-resistant strain), and cowpea Rhizobium K04SRPR (a phygon-resistant strain) were tested against Iroquois alfalfa (*Medicago sativa*), tendergreen bean (*Phaseolus vulgaris*), and whipporwill cowpea (*Vigna sinensis*), respectively. The alfalfa, bean and cowpea seedlings or plants were harvested when 6, 4, and 5 weeks old, respectively. Nodulation of each plant was evaluated by counting the number of pinkish nodules formed. Since numerous nodules were formed especially on the roots of alfalfa and beans, plus signs were used to depict the relative quantity of nodules in each case, as shown in Table 3. Nodules were formed in larger quantities on the roots of alfalfa and beans than on cowpea roots. However, all the strains of Rhizobium retained their ability to effect legume root nodule formation despite their fungicide-resistant characteristics.

TABLE 3

An Evaluation of the Nodulating Ability of the Fungicide-Resistant Strains of Rhizobium

| Strain of Rhizobium | Relative amount of nodules formed on host plant[a] |
|---|---|
| *R. meliloti* 87TR | ++++[b] |
| *R. phaseoli* 203CR | +++ |

TABLE 3-continued

An Evaluation of the Nodulating Ability of the
Fungicide-Resistant Strains of Rhizobium

| Strain of Rhizobium | Relative amount of nodules formed on host plant[a] |
|---|---|
| Cowpea Rhizobium K04SRPR | ++ |

[a]Seedlings of alfalfa inoculated with R. meliloti 87TR, bean inoculated with R. phaseoli 203CR, and cowpea inoculated with cowpea Rhizobium K04SRPR were harvested at the ages of 6, 4 and 5 weeks, respectively.
[b]++, +++, ++++, mean quantity of nodules formed in increasing degree.

EXAMPLE 5

Maintenance of Resistance Upon Plant Passage

The adapted strains of rhizobia were obtained from the nodules formed in the nodulation test of Example 4 and streaked onto a solid YEM medium. A single isolated colony was picked for streaking and repeated single-colony picking until uniformity of colony type was ascertained (Vincent, supra). A cell suspension (optical density 0.10 at 550 nm) of each re-isolated strain was later transferred to YEM broth containing the concentration of the fungicide to which the particular strain was resistant in order to determine if that strain still maintained its fungicide-resistant trait despite its passage through the host plant. In this way, the re-isolated R. meliloti, R. phaseoli, and cowpea Rhizobium were tested for growth in YEM media amended with 150 ppm thiram, 100 ppm spergon and 200 ppm phygon, respectively. On the fourth day of incubation on a shaker at 30° C., growth turbidity was observed visually. Of the 3 strains of rhizobia only cowpea Rhizobium K04SRPR had a streptomycin-resistant trait. Hence this re-isolated cowpea Rhizobium strain was tested for growth in a YEM medium containing 1,000 rpm of streptomycin sulfate by visually determining growth turbudity after four days of incubation on a rotary shaker at 30° C. The streptomycin sulfate was obtained from Schwartz/Mann, Division of Becton Dickinson and Co., Orangebury, N.Y. In each of the above experiments, control treatments were set up by adding the appropriate amount of fungicide or antibiotic to 50 ml of YEM prepared in 125-ml Erlenmeyer flask which was left uninoculated but incubated on the same shaker for four days. A conspicuous growth turbidity was observed in each flask inoculated with Rhibozium whereas the uninoculated control flasks showed no growth turbidity. Hence, after passing through the host plant once, the re-isolated strains still grew at concentrations of the fungicides inhibitory to their respective parent strains.

EXAMPLE 6

Confirmation of Identity of Fungicide-Resistant Strains

In spite of all the aseptic techniques employed during the process of adapting these strains of rhizobia to fungicides, the rhizobial cultures might have been contaminated. Hence, in order to determine if the fungicide-tolerant strains were still rhizobia, a comparative enumeration of the adapted strains was performed using two different methods. One method involved serial dilutions and plate counts, and the other was a most probable number (MPN)-plant infection technique. A closeness or a similarity of rhizobial counts from the two different methods of quantification would be taken as a presumptive evidence that the fungicide-tolerant strains were not contaminants. The plate count method of Vincent, supra, was used. Each fungicide-resistant strain was grown in YEM broth for four days at 30° C. and 1.01 ml portions of each cell suspension used for serial dilution in dilution bottles containing sterile distilled water. Appropriate aliquots, 1.0 or 0.1 ml, from each dilution bottle were aseptically introduced into a petri dish and the sample later thoroughly mixed with 20 ml of a melted, cooled YEM agar. Each petri dish was then incubated at 30° C. for three days, after which the Petroff Hausser bacterial counter was used to estimate the number of bacteria on each plate. The indirect plant infection count was performed according to the method of Vincent, supra. This method depends on the ability of a specific Rhizobium to produce nodules on an appropriate host legume, and assumes that a single Rhizobium cell added to the test plant leads to a sufficient population in the root surrounding to cause nodulation. The numbers of tubes with nodulated plants can then be used to determine the likely number of rhizobia in the suspension under test. Adapted strains of R. meliloti, R. phaseoli, and cowpea Rhizobium were tested for root-nodule formation using seeds of Iroquois alfalfa, tendergreen bean, and whipporwill cowpea, respectively. Tenfold dilutions, from $10^{-1}$ to $10^{-8}$ of each strain were prepared as in the plate count described above. Control dilutions without rhizobia were also prepared. Earlier, $150 \times 20$ mm tubes containing 8.0 ml of seedling agar (Vincent, supra) had been prepared and sterilized. One or two sterilized seeds were planted in each tube and 0.2 ml of each serial dilution used to inoculate the appropriate tube. The tubes were then incubated in cabinet incubators (Thelco, Model 16) maintained at about 26° C. The seedlings were illuminated with a 40-watt fluorescent lamp for about 16 hours a day at a temperature of 26° C. and kept in darkness for about 8 hours a day at a temperature of 22° C. The plants were harvested and examined for nodulation when they were about five weeks old. An enumeration of the adapted strains grown in YEM broth for three days using a plate count method as well as a plant infection-MPN techniques yielded similar counts (Table 4).

TABLE 4

Counts of the Fungicide-Tolerant Strains of
Rhizobium by Means of Plate Count
and Plant Infection-MPN Techniques

| | No. of Rhizobia/ml of Medium $\times 10^6$ | |
|---|---|---|
| Rhizobium Strain | Plate Count | Plant Infection-MPN Count |
| R. meliloti 87TR | 8.4 | 160 |
| R. phaseoli 203CR | 6.1 | 2.8 |
| Cowpea Rhizobium K04SRPR | 6.2 | 1.4 |

This closeness of counts was taken as a presumptive evidence that the adapted strains were rhizobia and not contaminants.

EXAMPLE 7

Cultural Characteristics of Sensitive and Resistant Strains

Nodulation of a host legume under bacteriologically controlled conditions is considered a most important means of authentication of a Rhizobium strain. However, certain cultural characteristics common to most rhizobia are considered complementary evidence for authentication of a rhizobial isolate. Hence, both the resistant and the sensitive or parent strains were examined for morphological and staining characteristics; growth with gum production on YEM agar; and growth in litmus milk and in peptone glucose agar (Difco) after two days at 30° C. An examination of the cultural characteristics of the adapted strains (grown on YEM agar for three days) showed that they were gram-negative short rods. Their colonies on YEM agar were as gummy as those of their parent strains, and they grew poorly with little or no change of pH in both litmus milk and in peptone glucose agar (Difco) after two days incubation at 30° C.

EXAMPLE 8

Greenhouse Investigation

After it has been found that the fungicide-resistant isolates were indeed rhizobia and that they were still infective and effective, it was considered of significance to: (a) apply these strains of rhizobia as well as their parent strains to the appropriate host seeds which had been previously treated with a reasonably high concentration of the appropriate fungicide; (b) find out if the fungicide-tolerant strains would maintain this trait on treated seeds and still cause legume nodulation; and (c) determine if the parent strains would fail to survive on treated seeds.

Preparation of Sand The sand samples were obtained from Syracuse Lumber Supplies, Syracuse, N.Y. The coarse quartz sand had an average diameter of 0.5 mm, and the fine quartz sand had an average diameter of 0.2 mm as estimated by passing through sieves of different mesh sizes. The sand samples were washed three times with hot water, soaked in water overnight, and finally rinsed with three changes of distilled water. This washing treatment raised the pH of the sand from 6.0 to 7.2 as determined in a 1:1 sand:water suspension using a Beckman pH meter. Eighty parts of the fine sand were mixed with 20 parts of the coarse sand in a clay pot that was 14 cm in diameter at the top, 8 cm in diameter at the bottom and 13 cm deep. A cotton plug was placed in the small hole at the bottom of each pot. For each set of experiments, 56 pots, filled ¾ full with this sand mixture, were prepared. The sand mixture had a water holding capacity of about 20% as measured gravimetrically (Gardiner, in "Methods of Soil Analysis", Black et al (ed.); *Agronomy* 9:82-127, Am. Soc. Agron., Madison, Wis., 1965). Each sand sample contained in a clay pot was moistened with distilled water, tightly covered with aluminum foil, and autoclaved for 12 hours at 121° C. and 15 lb pressure. After cooling, the pots were set on a 3 m$^2$ greenhouse bench that had been previously washed with warm water and disinfected with 5.2% aqueous solution of sodium hypochlorite (Clorox).

Plant Nutrient Solution. Bond's modified Crone's nitrogen-free nutrient solution was prepared as described by Allen, "Experiments in Soil Bacteriology", Burgess Pub. Co., Minneapolis, Minn. (1957).

Experimental Design. A factorial experimental design set up as a randomized complete block was used. The seed treatments were: (1) treated wtih fungicide and inoculated with fungicide-sensitive parent rhizobia; (2) treated with fungicide and inoculated with fungicide-tolerant rhizobia; (3) treated with fungicide but with no rhizobial inoculation; (4) not treated with fungicide but inoculated with fungicide-sensitive rhizobia; (5) not treated with fungicide but inoculated with fungicide-tolerant rhizobia; (6) treated with neither fungicide nor rhizobia; and (7) seeds with neither fungicide nor rhizobia but amended with 0.05% KNO$_3$ solution.

There were 8 replications of each of the seven treatments.

Treatment of Seeds with Chemicals. Iroquois alfalfa, tendergreen bean, and whipporwill cowpea seeds were used for testing the effectiveness of *R. meliloti* strains 87 and 87TR, *R. phaseoli* 203 and 203CR, and cowpea Rhizobium strains K04SR and K04SRPR, respectively. Thiram in dry powdered form was applied to slightly moistened alfalfa seeds at a rate of 5.0 mg/g seed. Similarly, spergon was applied to bean seeds at a rate of 5.1 mg/g and phygon to cowpea seeds at a rate of 1.3 mg/g. U.S. Environmental Protection Agency (EPA) recommends that field rates of these seed protectants for the appropriate legume seeds are 4 oz/100 lb seed (or 2.5 mg/g) for thiram, 4.1 oz/100 lb seed (or 2.55 mg/g) for spergon, and 1 oz/100 lb seed (or 0.65 mg/g) for phygon (Arneson, "Fruit Disease Control Recommendations for New York State", in "New York State Insecticide, Fungicide, and Herbicide Recommendations", Cornell Univ., 1975). Twice the concentration of fungicide recommended by EPA was used in this study to maximize contact of the applied rhizobia with the seed protectants, because a few fungicide-sensitive cells that are not affected by the chemical might multiply rapidly to form nodules and thus give erroneous results. The fungicide-treated seeds were left at room temperature for about two hours to allow the seeds to dry before inoculation.

Preparation and Application of Rhizobia Inoculants. A Rhizobium inoculate in peat carrier was prepared as follows: Each strain of Rhizobium was introduced into 600 ml of YEM broth prepared in 1 liter Erlenmeyer flask. The flask was then agitated on a rotary shaker (operating at a speed of 180 rpm) for three days at 30° C. After 3 days of incubation, each culture was centrifuged at 8,000$\times$g for 10 mins., and the pellets washed three times with 0.1 M phosphate buffer. After the last centrifugation, the pellet was resuspended in 10.0 to 20.0 ml of phosphate buffer to give a thick suspension of Rhizobium containing approximately $1.0 \times 10^9$ cells/ml. Each culture was added to sterilized commercial peat moss at the rate of 1.0 ml/g of peat. The peat moss which has a pH of 7.0 as determined in a 1:1 peat:water suspension, was autoclaved at 121° C. and 15 lb pressure for 30 mins. The peat moss was obtained from Agway Co., Ithaca, N.Y. The Rhizobium culture in peat carrier was incubated at 30° C. for four days to allow the culture to mature or the cells to further multiply and minimize later loss of viability. The rhizobia-containing peat moss had an approximate moisture content of 50%. The peat culture was applied to the fungicide treated or untreated seeds of alfalfa, bean, and cowpea at the rate of about 10 g/kg seed. The rhizobia-carrier was mixed thoroughly with the seeds in a 150$\times$15 mm plastic petri dish to ensure a complete coating of the seeds with the peat culture.

After the seeds had been treated in the 7 different ways described above, they were planted in the appropriate pots about 0.6 cm below the sand surface. Alfalfa seeds were introduced into the sand at the rate of about 20 seeds per pot, and bean and cowpea were planted with the hilum down at the rate of about 5 and 7 seeds per pot, respectively. Sterilized forceps were used for the planting. Each pot remained covered with aluminum foil until about 4 days after seedling emergence.

Care for Growing Plants. Each pot was carefully watered with sterilized distilled water and nutrient solution through one side of the pot to avoid splattering.

Distilled water at a rate of about 20 ml per pot was added once or twice a day, depending on the stage of plant growth and the greenhouse temperature. Sterilized nutrient solution was added twice a week at a rate of about 15 ml per pot. In addition, the nitrate pots received about 10 ml per pot of a 0.05% solution of $KNO_3$ twice a week. Any excess solution that drained out of the pot through its cotton-stoppered bottom hole collected in the large plastic petri dish placed underneath each pot, and this solution was added back to the sand culture by the following day. The greenhouse temperature was maintained at about 26° C. and 22° C. during the day and night, respectively. The greenhouse bench and floor were disinfected with Clorox each week. After emergence and full establishment of the young plants, the alfalfa seedlings were thinned to about 10 per pot, the bean and cowpea seedlings to 1 or 2 per pot. The plants were given 8 to 12 hours of supplemental overhead lighting using metal Hay Lit lamps (1000 watts).

Harvesting and Examination of Plants. The alfalfa, bean, and cowpea plants were harvested when 66, 32, and 49 days old respectively. To harvest the plants, sand from each pot was removed with a stream of water, and the plants were gently withdrawn to prevent damage to the nodules. The roots were then floated in water to allow for an examination of the presence, quantity, size, pigmentation, and location of the nodules. The aerial portion of the plant was also observed for chlorosis, vigor of stem and height of plant. The harvested plants were placed on paper towels and dried in air for four days. The plants were then dried in an oven for three days at 70° C. and the dry weight of each recorded. Each plant sample was later ground with a Wiley mill to pass a 2-mm mesh sieve. Total N analysis of the plant material was performed using the method of Jones, "Laboratory Procedures for the Analysis of Soils, Feed, Water, and Plant Tissue", Soil Testing and Plant Analysis Laboratory, Univ. of Georgia (1971).

Results. Both the dry weight and the N content of alfalfa plants whose seeds were treated with thiram prior to inoculation with the parent *R. meliloti* seemed to be considerably lower than those of plants derived from similarly thiram-treated seeds which were inoculated with thiram-resistant strain of *R. meliloti* (Table 5).

TABLE 5

Dry Weight and N Content of 66-day Old Alfalfa (*Medicago sativa*) Whose Thiram-Treated Seeds Were Inoculated with Thiram-Tolerant or Sensitive Strains of *R. meliloti*

| Treatment | No Fungicide | Fungicide Treated |
|---|---|---|
| | Dry Weight of Plants, g | |
| Sensitive *R. meliloti* 87 | $0.44^b$ | $0.28^a$ |
| Tolerant *R. meliloti* 87TR | $0.50^b$ | $0.49^b$ |
| Uninoculated alfalfa | $0.29^a$ | $0.27^a$ |
| Nitrate-amended alfalfa | $0.58^b$ | — |
| | N Content of Plants, mg | |
| Sensitive *R. meliloti* 87 | $12.2^d$ | $6.6^c$ |
| Tolerant *R. meliloti* 87TR | $14.6^d$ | $13.2^d$ |
| Uninoculated alfalfa | $6.8^c$ | $5.9^c$ |
| Nitrate-amended alfalfa | $16.8^d$ | — |

Values followed by a common letter are not significantly different at 5% level (Duncan's multiple range test). Each value represents a mean of 8 replications. The chemically treated seeds inoculated with the sensitive *R. meliloti* gave rise to weak seedlings and stunted plants whose leaves were chlorotic. Hence, the fungicide-sensitive wildtype seemed to have been deleteriously affected by the antifungal seed protectant, resulting in nodulation failure and poor dry matter yield. The nitrogen content of fungicide-amended plants inoculated with thiram-sensitive Rhizobium was only 50% of that of the treated plants inoculated with the adapted Rhizobium, and the N level was as low as that of the uninoculated alfalfa. On the other hand, the dry weight as well as the N contents of thiram-treated plants whose seeds were inoculated with thiram-tolerant strains were as high as the values for similarly inoculated plants which did not receive the fungicide treatment.

There was no statistically significant difference in the amounts of $N_2$ fixed symbiotically by bean plants whose seeds were inoculated with spergon-resistant *R. phaseoli* whether or not the seeds were treated with spergon prior to inoculation (Table 6). On the other hand, the quantity of $N_2$ fixed as well as dry weight of plants was reduced by about 50% if the treated seeds were inoculated with the spergon-sensitive *R. phaseoli* parent as compared to the resistant Rhizobium. The fungicide-treated beans inoculated with the unadapted strain of Rhizobium lacked nodules and consequently developed weak stems and chlorotic leaves. These observations of poor stem and leaf development were similar to those of uninoculated bean plants; suggesting an adverse effect on spergon on the unadapted strain of *R. phaseoli*.

TABLE 6

Yield of Beans (*Phaseolus vulgaris*) Whose Fungicide-Treated Seeds Were Inoculated With Spergon-Sensitive or Tolerant Strains of *R. phaseoli*

| Treatment | No Fungicide | Fungicide Treated |
|---|---|---|
| | Dry Weight of Plants, g | |
| Sensitive *R. phaseoli* 203 | $1.89^c$ | $0.99^b$ |
| Tolerant *R. phaseoli* 203CR | $2.19^c$ | $2.07^c$ |
| Uninoculated plant | $0.52^{ab}$ | $0.39^a$ |
| Nitrate-amended plant | $2.42^c$ | — |
| | Total N Content of Plants, mg | |
| Sensitive *R. phaseoli* 203 | $59.0^f$ | $30.7^d$ |
| Tolerant *R. phaseoli* 203CR | $67.7^f$ | $60.8^f$ |
| Uninoculated plant | $14.9^d$ | $12.3^d$ |
| Nitrate-amended plant | $92.5^e$ | — |

Values followed by the same letters are not significantly different at 5% level (Duncan's multiple range test). Each value represents a mean of 8 replications.

The dry matter yield and total N contents of cowpea plants whose seeds were treated with phygon prior to inoculation with phygon-sensitive or tolerant rhizobia followed the same trends observed with the treated alfalfa and bean plants. The sensitivity of the parent cowpea Rhizobium strain to phygon resulted in nodulation failure and low dry matter yield because the seeds receiving phygon prior to inoculation with parent rhizobia gave only 38% of the N yield as compared to the plants receiving no phygon treatment but inoculated with the same sensitive strain (Table 7). Apparently, the phygon treatment of cowpea seeds did not affect the nodulating ability of the cowpea Rhizobium strain previously adapted to the fungicide, for there was no significant difference in yields between the plants amended with phygon and the ones with no phygon treatment prior to inoculation with this Rhizobium. In both treatments (treated and untreated seeds inoculated with the adapted strain of cowpea Rhizobium), the dry matter yields and N contents were as high as those of the nitrate-amended control treatment. The nodulated cowpea plants were relatively tall, vigorous, and bore large green leaves, whereas the plants lacking nodules were noticeably stunted and carried fewer leaves, most of which were chlorotic.

TABLE 7

Yield of 7 Week Old Cowpea (*Vigna sinensis*) Whose Seeds were Inoculated with Phygon-Sensitive or Resistant Strains of Cowpea Rhizobium

| Treatment | No Fungicide | Fungicide Treated |
|---|---|---|
| | Dry Weight of Plants, g | |
| Sensitive cowpea Rhizobium K04SR | 3.82[b] | 1.82[a] |
| Resistant cowpea Rhizobium K04SRPR | 3.79[b] | 3.93[b] |
| Uninoculated cowpea | 1.10[a] | 1.15[a] |
| Nitrate-amended cowpea | 4.34[b] | — |
| | N Content of Plants, mg | |
| Sensitive cowpea Rhizobium K04SR | 97.0[d] | 36.4[c] |
| Resistant cowpea Rhizobium K04SRPR | 106[d] | 105[d] |
| Uninoculated cowpea | 23.2[c] | 21.7[c] |
| Nitrate-amended cowpea | 146[e] | — |

Values followed by different letters are significantly different at 5% level (Duncan's multiple range test). Each value represents a mean of 8 replications.

EXAMPLE 9

Mechanisms of Fungicide Resistance

Testing of Detoxication Hypothesis. It was decided to study the possible role of detoxication processes in the apparent lack of sensitivity of the 3 strains of rhizobia to the respective antifungal agents, since the ability of a fungicide-tolerant strain of Rhizobium to detoxify the inhibitor might be the basis for its tolerance to the toxicant. A toxin-resistant cell may detoxify a bactericidal chemical by using the fungitoxicant as a nutrient, by converting it to a nontoxic compound, or by transforming the fungicide into a volatile compound which may then be lost from the culture.

1. Conversion of the Fungicides to Nontoxic Compounds. Each fungicide-tolerant strain of Rhizobium was incubated for 4 to 5 days in 50 ml YEM broth containing a concentration of the fungicide to which the test strain was tolerant but to which the parent strain was sensitive, namely 200 ppm thiram, 120 ppm spergon, and 400 ppm phygon for media inoculated with *R. meliloti* 87TR, *R. phaseoli* 203CR, and cowpea Rhizobium K04SRPR, respectively. Controls contained the same concentrations of the fungicides in YEM media, but solutions were not inoculated with rhizobia. The 125-ml Erlenmeyer flasks containing the inoculated and uninoculated media were incubated on a rotary shaker for five days at 30° C. At the end of the incubation period, each culture was centrifuged at 9,000×g for 10 mins., and the supernatant liquid was sterilized by filtering through 0.20 μm fluorocarbon Millipore filters. Portions of the sterilized fluid were added to 10 ml of YEM broth contained in 25-ml test tubes, and the tubes were inoculated with the appropriate sensitive parent strains. Eight milliliters, 15.0 ml, and 3.0 ml of the sterilized supernatant fluid containing 300 ppm thiram, 120 ppm spergon, and 400 ppm phygon, respectively, were withdrawn into 10.0 ml of YEM media to give concentrations of 88.9 ppm, 72.0 ppm, and 92.3 ppm, respectively, of the fungicides in the latter media. In the same experiment, controls consisting of unamended YEM inoculated with the parent cells were included. The test tubes were incubated on a rotary shaker operating at a speed of 120 rpm, at 30° C. In the case of thiram and spergon rhizobial growth turbidity was observed visually after two to three days of incubation, but in the case of phygon, growth of the parent strain was monitored turbidimetrically for a 36-hour period, using a Spectronic 20 spectrophotometer (Bausch and Lomb Rochester, N.Y.), and measuring optical density at 540 nm.

2. Chemical Assays for Fungicide Disappearance.

(a) Phygon. Fifty milliliters of YEM broth was introduced into each of seventy 125-ml Erlenmeyer flasks and autoclaved for 15 mins. at 121° C. Later, 14 of the flasks were inoculated with the cowpea Rhizobium strain K04SRPR, and the remaining 56 flasks were amended with 200 ppm phygon. Then, 28 of these fungicide-containing flasks were inoculated with 1.0 ml each of a diluted suspension (optical density of 0.2 at 540 nm as measured with a Spectronic 20 spectrophotometer) of washed cells derived from a 48-hour old culture of the cowpea Rhizobium K04SRPR, 14 of the flasks were each inoculated with washed cells of a 48-hour old culture of the fungicide-sensitive parent strain, KOSR, and the remaining 14 flasks were left as uninoculated controls. All flasks were incubated on a 180 rpm speed rotary shaker at 30° C. Samples were taken from 0 to 7 days by removing two flasks for each of the above treatments, and the solutions were either immediately extracted and analyzed for residual phygon or stored at −20° C. for later analysis.

Experiments identical to the one just described were performed to measure the concentration of thiram and spergon during incubation with *R. meliloti* 87TR and *R. phaseoli* 203CR, respectively.

For the extraction of residual phygon in 50 ml of the YEM broth in each flask, 20 ml of benzene was used for each of three extractions. Extraction was done by swirling the mixture of solvent and solution several times in a 250 ml separatory funnel. The contents of half of the flasks initially receiving 200 ppm phygon and Rhizobium K04SRPR were centrifuged at 9,000×g for 15 mins., and the phygon remaining in the supernatant fluid was determined separately from that in the pellet in order to assess if the toxicant had accumulated on or within the bacteria without necessarily being metabolized. Analysis of phygon in the benzene extracts was performed according to the method of Lane (1958). Addition of 10.0 ml of 10% aqueous dimethylamine to the benzene extract resulted in an intense orange coloration, which was proportional to the concentration of phygon in the extract (Lane, *J. Agric. Food Chem.* 6:746–747, 1958; Lane, "Phygon" in "Analytical Methods for Pesticides, Plant Grow Regulators, and Food Additives", Zweig (ed.), Vol 3: 144–150, Academic Press, N.Y., 1964). Colorimetric measurement of optical density was performed with a spectrophotometer, model-Spectronic 20, at a wavelength of 490 nm. The phygon concentration in each extract was determined from a standard curve. The experiment above was repeated using a chemically defined medium instead of YEM as the incubation medium.

(b) Thiram. YEM broth containing 100 ppm thiram in 125-ml Erlenmeyer flasks was inoculated with thiram-sensitive strain of *R. meliloti* 87 or the resistant strain *R. meliloti* 87TR, and some flasks were left as uninoculated controls. The experiments and the sampling were conducted exactly as described above for phygon. The thiram remaining in each flask was extracted three times with ⅓ volumes of chloroform and analyzed by a colorimetric method based on the formation of a yellow-brown, chloroform-soluble copper salt of dialkyldithiocarboamate when a chloroform solution of thiram was treated with CuI (Keppel, *J. Assoc. Off. Agric. Chem.* 39:708–712, 1956). The optical density was measured at 420 nm.

(c) Spergon. Experiments identical to the one described for phygon were conducted to determine the possible disappearance of spergon when YEM broth containing 200 ppm spergon was inoculated with spergon-tolerant *R. phaseoli* 203CR or spergon-sensitive *R. phaseoli* 203. The spergon remaining in the medium was extracted three times with ⅓ volumes of benzene and determined colorimetrically by measuring the intensity of the yellow-green color formed upon treating the spergon extract with anhydrous diethylamine (Lane et al, "Chloranil" in "Analytical Methods for Pesticides, Plant Growth Regulators, and Food Additions", Zweig (ed). Vol. 3:27–39, 1964). The optical density was measured at 450 nm.

As described above, the phygon-sensitive parent cowpea Rhizobium was unable to grow in 10.0 ml YEM amended with 3.0 ml portions of uninoculated, phygon-amended (400 ppm in 50 ml YEM broth) medium that had been incubated for 5 days. However, the same parent strain grew copiously in YEM broth amended with 3.0 ml portions of the supernatant liquid of phygon-treated YEM broth that had been incubated with phygon-tolerant strain of cowpea Rhizobium for 5 days (FIG. 1). In a similar experiment, the thiram-sensitive strain of *R. meliloti* grew luxuriantly in YEM medium amended with portions of the supernatant fluid derived from thiram-containing YEM in which the mutant *R. meliloti* had grown for 4 days. Similarly, the spergon-sensitive strain of *R. phaseoli* flourished in YEM broth treated with portions of the supernatant fluid derived from spergon-amended medium in which the spergon-tolerant *R. phaseoli* strain had been grown for 4 days. In the case of the thiram and spergon experiments, rhizobial growth turbidity was observed visually. Such proliferation of the sensitive strains in a potentially toxic medium suggested the detoxication of the fungicides by the tolerant strains of Rhizobium.

Figure 2:
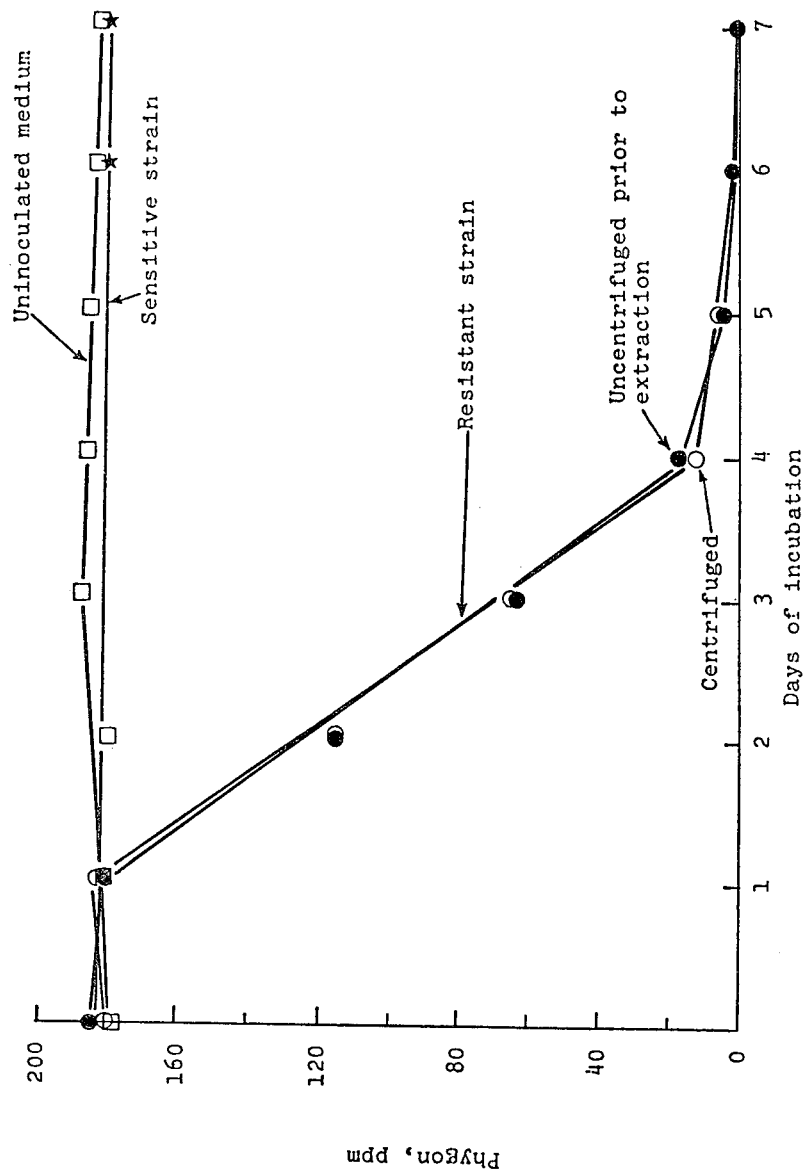
FIG. 2 shows the concentration of phygon in uninoculated YEM broth containing 200 ppm phygon and in the same medium inoculated with resistant or sensitive strains of cowpea Rhizobium. (See Example 9)
Figure 3:
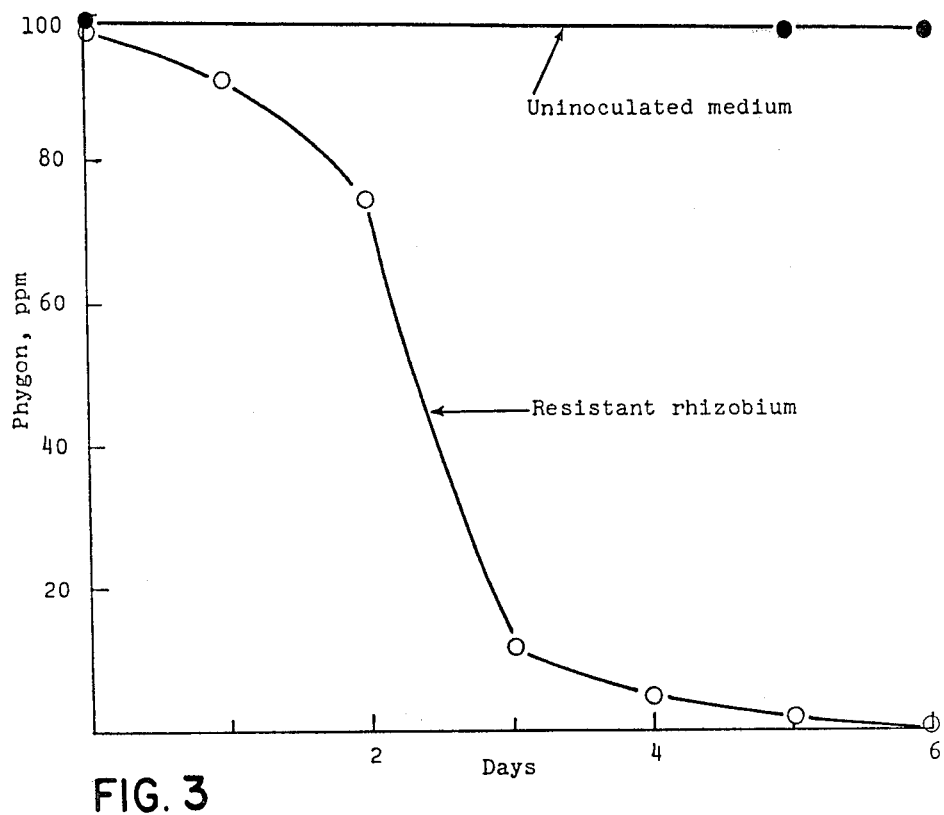
FIG. 3 shows the concentration of phygon in uninoculated mineral salts-mannitol medium amended with calcium panthothenate and in the medium inoculated with phygon-tolerant cowpea Rhizobium K04SRPR. (See Example 9)

Chemical Assays for Fungicide Disappearance. By the third day of incubating the phygon-tolerant strain of cowpea Rhizobium with 200 ppm of phygon in YEM broth only 30% of the initial concentration of phygon remained in the broth; and on the sixth day of incubation, approximately 1 ppm phygon was extractable from the medium (FIG. 2). The similarity of patterns of phygon disappearance in the treatment in which the resistant cells were centrifuged prior to a separate extraction of the pellets and supernatant portions and that in which phygon was extracted without any centrifugation of the cells nullified the hypothesis that the toxicant might have accumulated within or on the bacterial cells without being metabolized. The curve labeled "centrifuged" in FIG. 2 represents the sum of the quantity of phygon recovered from the cell paste plus that extracted from the supernatant liquid. The parent cowpea Rhizobium failed to grow at this high level of the fungicide, and the concentration of phygon in the medium inoculated with this sensitive strain remained unchanged as did the level in the uninoculated medium. It is evident from FIG. 3 that not all of the phygon was recovered from the incubation medium, probably because a small portion of the fungicide was lost to the aqueous layer during extraction. The concentration of phygon also decreased rapidly and considerably after inoculation of a defined, mineral salts medium (amended with 100 ppm phygon) with the phygon-tolerant strain of cowpea Rhizobium (FIG. 3). The disappearance of the antifungal chemical in a simple medium rules out the possibility of a complex formation between yeast extract and the fungicide as an important factor in its detoxication.

Figure 4:
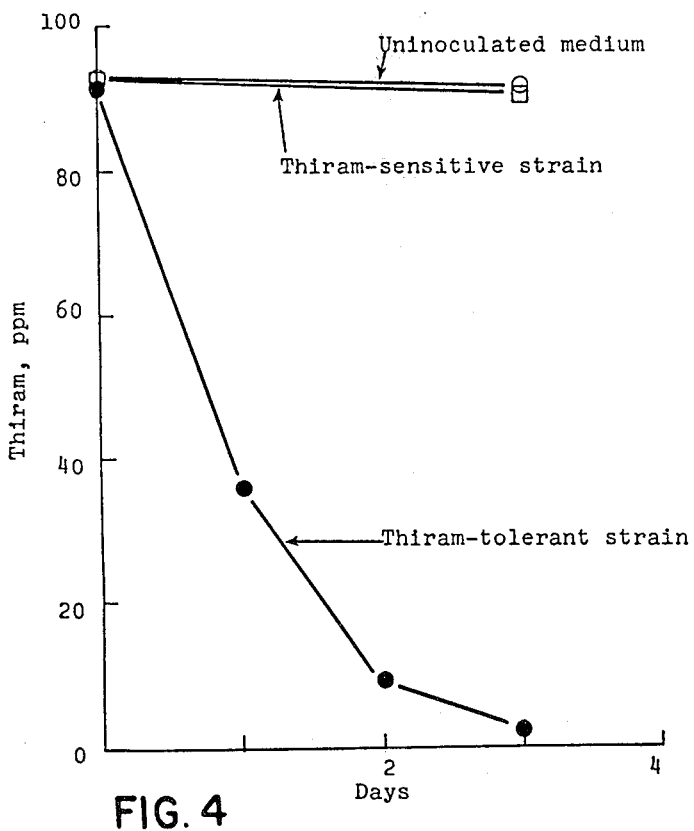
FIG. 4 shows the concentration of thiram in uninoculated mineral salts-mannitol medium amended with inositol (meso) and treated with 100 ppm of the fungicide and in the same medium inoculated with thiram-tolerant and sensitive R. meliloti. (See Example 9)

FIG. 4 shows a more than 60% loss in the initial concentration of thiram after only one day of incubation with a thiram-tolerant strain of *R. meliloti*. The concentration of the fungicide was reduced to 3 ppm by the third day of incubation. However, at the end of the experiment, the concentrations of thiram in the medium inoculated with thiram-sensitive *R. meliloti* and that of the uninoculated broth remained as they were at the beginning of the experiment.

Figure 5:
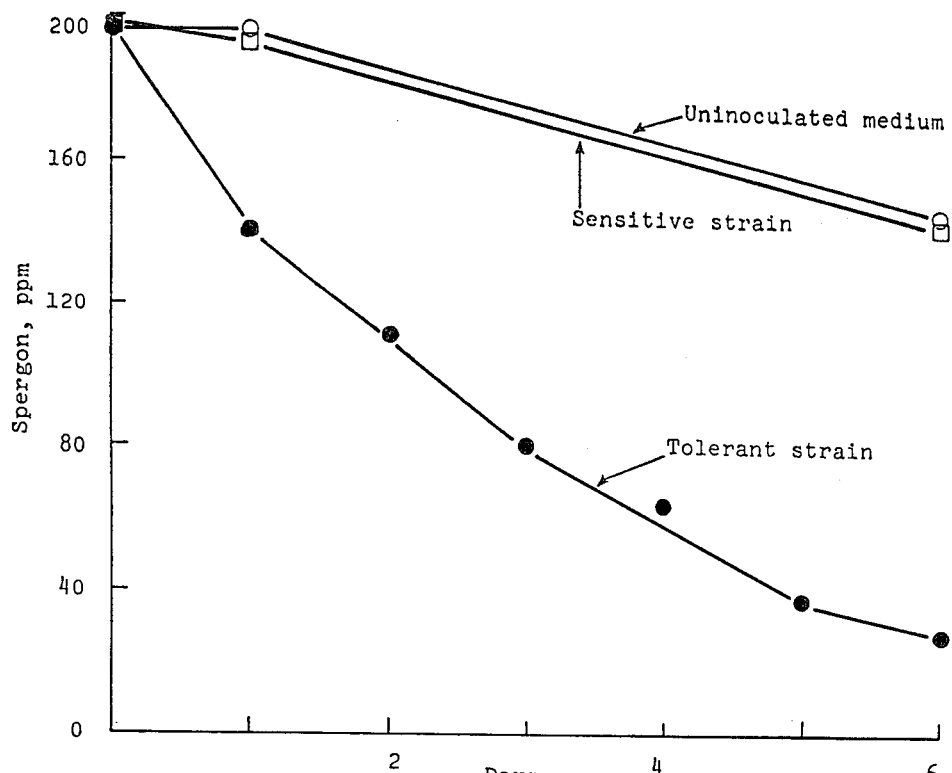
FIG. 5 shows the effect of spergon-resistant R. phaseoli 203CR and the parent strain on spergon disappearance. (See Example 9)

In the presence of the spergon-tolerant strain of *R. phaseoli*, the initial concentration of spergon in YEM broth (200 ppm) was reduced by 80% after 5 days of incubation (FIG. 5). However, a similar decrease in spergon concentration was not observed in the broth inoculated with the spergon-sensitive, parent *R. phaseoli*. Fig. 5 also depicts a slight decrease in the concentration of spergon in both the uninoculated medium and the broth inoculated with the wildtype strain of *R. phaseoli*. This decrease in the level of spergon after 6 days of incubation in YEM broth was probably a result of the instability of this compound due to photochemical breakdown or volatilization.

Figure 6:
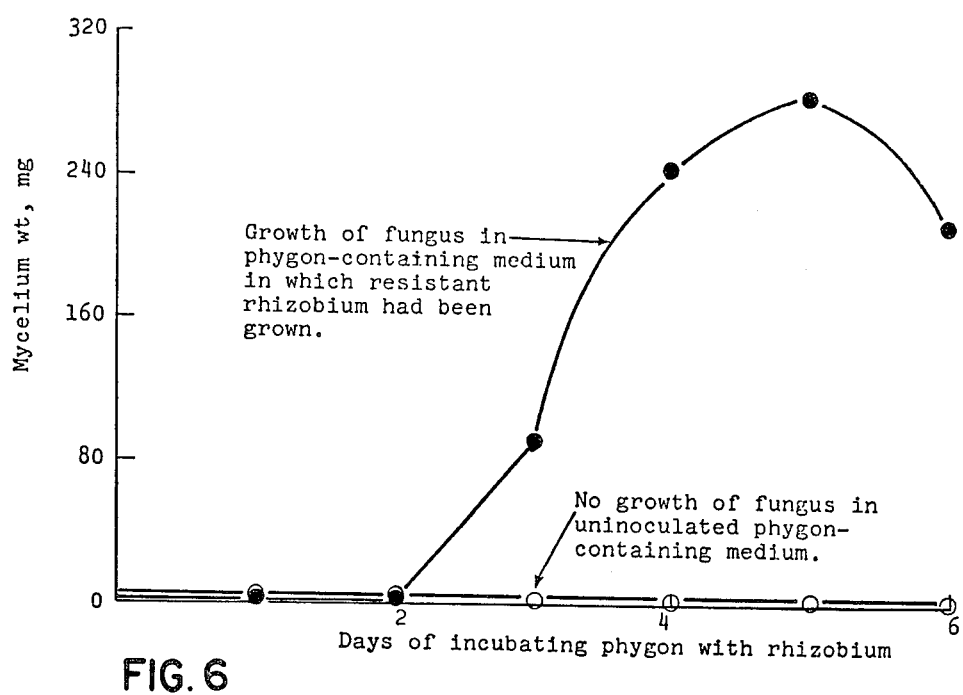
FIG. 6 shows Pythium bioassay to monitor phygon detoxication by cowpea Rhizobium K04SRPR. (See Example 9)

3. Bioassay of Phygon Detoxication. The test fungus used was *Pythium debaryanum* (a causal agent of many legume diseases), and it was obtained from Department of Plant Pathology, Cornell University. The fungus was grown on a Difco potato dextrose agar (PDA) medium contained in Roux bottles, for three weeks at 30° C. to allow for good sporulation. The spores were then harvested by pouring sterile distilled water into the bottle, shaking the bottle for several minutes, and decanting the spore-laden liquid into a sterile flask. This suspension was used for inoculation. Each of 14 125-ml Erlenmeyer flasks containing 50 ml of YEM broth that was amended with 100 ppm phygon was inoculated with phygon-resistant cowpea Rhizobium K04SRPR and incubated on a 180 rpm speed rotary shaker at 30° C. for seven days. The same number of flasks with YEM broth containing 100 ppm phygon were incubated without rhizobial inoculation. Portions (5.0 ml) were withdrawn daily from two flasks of each treatment, and each sample was introduced into 45 ml of potato dextrose broth (PDB) contained in 125-ml Erlenmeyer flasks, thereby yielding phygon in a concentration 1/10 that of the original. The latter medium was then supplemented with 50 ppm of the sodium salt of penicillin G (purchased from Schwartz/Mann, Division of Becton Dickinson and Co., Orangeburg, N.Y.) to inactivate the Rhizobium, and it was then inoculated with 2.0 ml of a spore suspension of *Pythium debaryanum*. The flasks were incubated on a rotary shaker (operating at 180 rpm) at 30° C. After seven days, each flask was steamed for about 10 mins. in an Arnold steamer to kill the fungal spores. The fungus pellets in each flask were then carefully harvested with forceps and placed in a tared weighing dish, which was then dried at 90° C. for 12 hours. The dry weight of the fungal mass was determined subsequently. The results are shown in FIG. 6. After 2 days of incubating the fungicide-tolerant cowpea Rhizobium strain in the medium with phygon, the chemical was not sufficiently detoxified to enable the fungus to grow in a medium treated with portions of the inoculated, fungicide-containing medium. However, on the third day of incubation, the concentration of the toxicant had been drastically reduced, probably to less than 4 ppm, by the adapted strain, thus enabling the fungus to grow. A product of phygon detoxication present on day 4 and day 5 seemed to be stimulatory to the growth of the fungus since the fungal weight of about 270 mg during this period was very much higher than the value of mycelial weight (180 mg) in the control medium devoid of fungicide. The fungus was unable to grow in a PDB medium amended with portions of the uninoculated phygon-treated broth.

A standard curve was also prepared to determine growth of *P. debaryanum* at different concentrations of phygon, and in this instance, the inoculation conditions were identical to that given above. It was noted that the growth of the fungus was strongly inhibited at a phygon concentration of more than 4 ppm. 4. Ultraviolet Absorption of Phygon Residues after Incubation with Rhizobium K04SRPR. To determine a probable change in UV-absorption of phygon resulting from its presumed degradation by the cowpea Rhizobium K04SRPR, the following experiment was performed. Fifty milliliters of YEM broth was prepared in each of thirty-two 125-ml Erlenmeyer flasks, sterilized, and then amended with 100 ppm phygon. Sixteen of the flasks were inoculated with washed cells from a 48-hour old culture of cowpea Rhizobium K04SRPR, and the other 16 were uninoculated. All of the flasks were incubated on a rotary shaker at 30° C. Samples from two inoculated and two uninoculated flasks were taken from 0 to seven days. Each 50-ml sample was extracted with 20 ml of benzene three times by swirling the mixture of solution and solvent several times in a 250 ml separatory funnel. The UV-absorption of the benzene extract was determined using a Beckman spectrophotometer, model DBG, and reading the absorbency at 276 nm. The UV-absorption of phygon as well as that of benzene was also determined in the entire range of ultra-violet wavelengths. The UV-absorption of the benzene extracts declined sharply after the first day of incubation. By the fifth day of the experiment, the concentration of phygon had become so low that its UV-absorption was almost negligible, whereas that of the uninoculated medium remained as it was at the beginning of the experiment. 5. Respirometric Technique to Assess Phygon Metabolism. Cowpea Rhizobium K04SRPR was grown in one liter of 0.5% mannitol-mineral salts broth contained in a 2-liter Erlenmeyer flask which was incubated on an NBS gyrotory shaker (New Brunswick Scientific Co., New Brunswick, N.J.) operating at 180 rpm for 48 hours at 30° C. Resting cells were obtained by centrifuging the culture at 8,000×g for 10 mins. in a Sorvall RC 2-B refrigerated centrifuge. The cells were suspended in 0.1 M phosphate buffer of pH 7.0 and washed four times to remove the supernatants containing any residual substrates and ensure a thorough washing of the cells. The resulting cells were incubated in 0.1 M phosphate buffer (pH 7.0) for 1 hour on a rotary shaker at 30° C., to reduce the rate of endogenous respiration. The cell density was 10.2 as measured by a spectrophotometer (Spectronic 20) at a wavelength of 550 nm. Standard Warburg manometric techniques, as described by Umbreit et al, "Manometric and Biochemical Techniques", 5th ed., Burgess Pub. Co., Minneapolis, Minn. (1972), were used to determine $O_2$ uptake by the Rhizobium. Two micromoles of phygon prepared in 0.5 ml of acetone was introduced into the main vessel of a Warburg flask, and the acetone evaporated off in a stream of nitrogen. This main compartment also received 2.5 ml of 0.1 M phosphate buffer (pH 7.0). The side-arm of the flask contained 0.5 ml of a resting cell suspension, and the center well received 0.2 ml of 20% KOH. The liquid volumes of the flask were maintained at 3.2 ml. Endogenous respiration and respiration in the presence of phygon were conducted in duplicate. The temperature of the water bath of the respirometer was kept at 30° C. Readings of manometric $O_2$ consumption were taken at 30 minute intervals for 7½ hours. Compared to the cells' endogenous respiration, $O_2$ consumption by the cowpea Rhizobium was substantially enhanced in the presence of the fungicide. For instance, the $O_2$ consumption increased from 2.4 mmol during the first hour of incubation to 11 mmol after 5 hours (after correcting the values for endogenous respiration).

Nutritional Requirements of Rhizobia. In order to study the metabolism of these antifungal chemicals by the fungicide-tolerant strains, it was necessary to replace the complex, yeast extract-containing YEM medium with a simple mineral salts medium amended with only one or two growth factors. Consequently, a modified Vincent's, supra, mineral salts medium containing the following macro- and macro-nutrients per liter of distilled water was prepared: 10.0 g mannitol, 1.0 g $K_2HPO_4$, 1.0 g $KH_2PO_4$, 1.0 g $KNO_3$, 0.2 g $NaH_2PO_4.2H_2O$, 0.18 g $MgSO_4$, 0.13 g $CaSO_4.2H_2O$, 0.10 g $Fe(NO_3)_2.9H_2O$, 0.2 mg $NaMoO_4.2H_2O$, 0.2 mg $ZnSO_4.7H_2O$, 0.2 mg $H_3BO_3$, 0.2 mg $MnSO_4.H_2O$, 0.015 mg $CuSO_4$, and 0.001 mg $Co(NO_3)_2.6H_2O$. Portions (15.0 ml) of this mineral salts-mannitol medium were placed in 25 ml test tubes, and 7 of these tubes were amended with 1.3 mg/l of each of the following seven vitamins: p-aminobenzoic acid, pyridoxine phosphate, inositol(meso), thiamine mononitrate, calcium pantothenate, riboflavin, and biotin. The growth factors were obtained from Nutritional Biochemicals Corp., Cleveland Ohio. Each tube was then inoculated with 0.1 ml of a cell suspension derived from a 48-hour culture of the rhizobia that had been washed three times with 0.1 M phosphate buffer (pH 7.0). The cell density was 0.10 as measured by a spectrophotometer, model Spectronic 20, at a wavelength of 540 nm. Controls consisting of inoculated and uninoculated mineral salts-mannitol media were also prepared. Each treatment was in duplicate. All the tubes were incubated on a rotary shaker at 30° C. for two days, with a shaker speed of 180 rpm. Growth of bacteria in each tube was measured turbidimetrically at intervals of three hours using a spectrophotometer (Spectronic 20), and measuring optical density at 540 nm. As shown in Table 8, the adapted cowpea Rhizobium strain K04SRPR grew well in a mineral salts-mannitol medium amended with calcium pantothenate, whereas growth was somewhat slower in the same medium treated with other growth factors or with no vitamins. Thiram-tolerant *R. meliloti* 87TR grew readily in the mineral salts-mannitol broth amended with inositol(meso) or pyridoxine phosphate, while spergon-ressitant *R. phaseoli* 203CR grew reasonably well when the medium was treated with either calcium pantothenate or thiamine mononitrate. Growth turbidity was observed visually in the case of *R. meliloti* 87TR and *R. phaseoli* 203CR.

TABLE 8

Generation Time of Cowpea Rhizobium K04SRPR in 0.5% Mannitol-Mineral Salts Medium Amended With Different Growth Factors

| Vitamin Added | Generation Time, Hr. |
|---|---|
| Calcium Pantothenate | 4.5 |
| Thiamine Mononitrate | 5.4 |
| Biotin | 5.4 |
| Riboflavin | 5.4 |
| Inositol (meso) | 5.4 |
| Pyridoxine Phosphate | 6.0 |
| p-Aminobenzoic Acid | 6.6 |
| Mineral Salts-Mannitol Alone | 6.6 |

EXAMPLE 10

Metabolism of the Fungicides

Metabolism of phygon. Cowpea Rhizobium K04SRPR was grown in one liter of 0.5% mannitol-mineral salts broth contained in a 2-liter Erlenmeyer flask which was incubated on a rotary shaker (revolving at 120 rpm) for 48 hours at 30° C. Resting cells were obtained by centrifuging the culture at 8,000×g for 10 mins. in a Sorvall RC 2-B refrigerated centrifuge. The cells were suspended in 0.1 M phosphate buffer (pH 7.0) and washed four times to free the cells of any residual mannitol. The cells were resuspended in phosphate buffer and diluted with the buffer to give an optical density of 10.4 as measured by a spectrophotometer, model Spectronic 20, at a wavelength of 550 nm. This cell suspension was introduced into 450 ml of 0.1 M phosphate buffer containing 600 ∥ mol of phygon in a 1-liter Erlenmeyer flask. A flask containing 600 μmol of phygon in buffer and another containing only the Rhizobium cells in phosphate buffer were also prepared. The flasks were incubated on a rotary shaker (revolving at 180 rpm) at 30° C. for 4.5 hours in one experiment and for 2 hours in another. The supernatant fluid of each flask was separated from the cells by centrifuging the growth medium at 8,000×g for 10 mins. Portions of the supernatant fluid were tested qualitatively for the release of chloride ions from the chemical. For this purpose 5.0 ml of the liquid was treated with a few drops of 0.1 N $HNO_3$ and 2.0 ml of 1.0% aqueous solution of $AgNO_3$. If chloride was present, a white precipitate or turbidity would appear, the intensity of the response depending on the quantity of chloride (Feigl, "Spot Tests in Inorganic Analysis", Elsevier Pub. Co., Amsterdam 1958). The remaining liquid and the cell pellets were acidified to pH 2.0 with concentrated HCl to inactivate the microorganisms. The cell pellets and the supernatant fluids were subjected to three ether and then two hexane extractions using two volumes of solvent to one of cell paste and ⅓ volumes of ether or hexane for the supernatant liquid. Extraction was performed by shaking the mixture of solvent and solution several times in a 1-liter separatory funnel. The extracts were then collected in 500-ml Erlenmeyer flasks and the volume of each extract was reduced to about 15 ml by means of a rotary flash evaporator. The concentrated extracts were then stored at 4° C. pending further analysis.

Thin-Layer Chromatography. Thin-layer chromatography of phygon-decomposition products obtained from 4.5 hours incubated cells was performed by using 20×20 cm Chromagram sheets coated with silica gel containing a fluorescent indicator exiciting at 254 nm. The samples were spotted on the thin-layer plates by using a 10 μl syringe. The spotted plate was then put into a chromatography tank saturated with 150 ml of a solvent mixture of toluene-hexane-ethyl formate-ethanol (5:2:2:1). A solution of authentic phygon (0.001%) in ether was also spotted on each plate as a standard. The plate remained in the tank for about 60 mins. before being air-dried. Visualization of the various spots corresponding to phygon degradation products was accomplished by placing the plate under a short-wave (254 nm) UV-lamp. The color and the $R_f$ value of each spot were recorded.

| Color and $R_f$ Values of Five Different Products Formed from Metabolism of Phygon by Cowpea Rhizobium K04SRPR | | |
|---|---|---|
| Product | Color | $R_f$ Value* |
| A | Intense Yellow | 0.07 |
| B | Dark Brown | 0.19 |
| C | Orange Brown | 0.36 |
| D | Whitish | 0.45 |
| E | Light Yellow | 0.97 |

*Chromatogram was developed with a solvent mixture of toluene hexane-ethyl formate-ethanol (5:2:2:1); and the colors were observed under a short-wave (254 nm) UV-lamp.

The orange brown product (metabolite C) was obtained from 600 μmol phygon was incubated with the Rhizobium for only 2 hours. Product (C) had a melting point of 159°-160° C. as determined by using a Nagle hot plate microscope. The melting point of spergon is 193° C. The infrared spectra on KBr mini-pellets of phygon and product (C) were obtained. A comparison of the two spectra shows a conspicuous strong band at 3520-3100 $cm^{-1}$ in the spectrum of product (C), and this band is not present in the spectrum of phygon. The strong band probably corresponds to associated hydroxyl groups. The presence of hydroxyl groups in metabolite (C) might have resulted from the bacterial reduction of carbonyl groups of phygon to hydroxyl groups. Most of the absorption bands present in the parent compound are missing from the spectrum of the presumed product (C). Such absorption bands in the spectrum of phygon are (a) the very strong band at 1700-1600 $cm^{-1}$ which probably corresponds to aryl carbonyl groups and (b) the medium band at 1590 $cm^{-1}$ which probably corresponds to the vibrations of phenyl ring conjugated carbon-carbon double bonds. There is an unidentified strong band in the spectrum of metabolite (C) at 1000 $cm^{-1}$ which seems to correspond to that of a $CH=CH_2$ group. This band is also not seen in the spectrum of phygon. The above infrared spectral observations suggested as extensive destruction of the parent molecule of the Rhizobium to form the metabolite (C). The chemical ionization mass spectrum of metabolite (C) was obtained on a Finnigan-3300 quadrapole mass spectometer using $CH_4$ as a reagent gas. The molecular weight of metabolite (C) was determined to be 182. The molecular weight of phygon is 226.

Metabolism of Spergon. R. phaseoli 203CR was incubated with 600 μmol of spergon for 4 hours, and the products of spergon metabolism extracted with ether and hexane. A quantitative analysis of chloride ions in the reaction medium revealed that approximately 195 ug/ml chloride ions were formed from 1,000 ug/ml spergon by the Rhizobium, and this quantity of chloride ions accounts for about ⅓ of the total chlorine present in the spergon supplied. Thin-layer chromatographic analysis of the extracts showed that the golden yellow fungicide had been converted to a lavender-colored fluorescing compound. When a chromatogram containing this compound was developed with a solvent mixture of toluene-benzene-ethyl acetate-acetic acid (50:40:40:10), this product was found to have an $R_f$ value of 0.87. There was no further identification or characterization of this product.

The condensed extract of the phygon-containing broth incubated with phygon-tolerant Rhizobium for only two hours was subjected to TLC analysis as described above and then to a preparative TLC. To separate the products on a preparative scale, 2-mm thick silica gel with ultraviolet (254 nm) indicator coated on 20×20 cm glass plates (Brinkman Instrument Co., Westbury, N.Y.) was used. The thick-layer plate was streaked with sample solutions by means of a Pasteur pipette. The plate was then transferred to a chromatograph tank containing a solvent mixture of toluene-hexane-ethyl formate-ethanol (5:2:2:1). After about 60 mins., the plate was removed from the tank, air-dried for about 30 mins. and then put back into the tank. In this way, the solvent was allowed to migrate through the layer four times with an air-drying of the plate between each migration. The clearly separated band on the plate was scrapped off with the silica gel into a 250-ml separatory funnel, and it was extracted four times each with 15.0 ml of ether and then 15.0 ml of hexane. The extract was concentrated in a rotary flash evaporator to a volume of about 10 ml and then filtered through Whatman No. 42 filter paper into a 50-ml Erlenmeyer flask. This solution was further concentrated by evaporating off the solvent in a stream of clean, dry nitrogen. About 5 ml of ethanol was added to the resulting crude crystalline material and the flask kept for about 6 days inside a laboratory refrigerator at 4° C.; during this time period the presumed product of phygon metabolism crystallized from ethanol. The crystals were carefully collected, air-dried, and stored in a small stoppered bottle at 4° C. To check or confirm the purity of the product, a small portion of the crystals was dissolved in 2.0 ml of ether and spotted on a TLC plate identical to the one described earlier. The plate was then placed in a separation tank containing the same solvent mixture used earlier.

Melting Point Determination. The melting point of the crystalline product was determined by using a Nagle hot plate microscope and the melting point value obtained was corrected for the instrumental error.

Infrared Spectra. Infrared spectra of the product of phygon metabolism and the authentic phygon were obtained on a Beckman IR-10 double-beam infrared spectrophotometer. The samples were prepared as KBr mini-pellets, using 5 mg of chemical in 100 mg of KBr (Spectrographic grade from International Crystal Laboratories, Irvington, N.J.).

Mass Spectra. Chemical ionization mass spectra of product (C) formed from phygon were obtained in a Finnigan-3300 quadrapole mass spectrometer. $CH_4$ was used as the reagent gas. Samples were introduced via a heated probe inserted directly into the ion source.

Metabolism of Spergon. *R. phaseoli* 203CR was grown in one liter of 0.5% mannitol-mineral salts broth contained in a 2-liter Erlenmeyer flask which was incubated on a rotary shaker for 48 hours at 30° C. Washed resting cells were obtained from the culture as described in the studies of phygon metabolism. A suspension of the resting cells in 0.1 M phosphate buffer (pH 7.0) gave an optical density of 9.8 as measured by a spectrophotometer (Spectronic 20) at a wavelength of 550 nm. This cell suspension was introduced into 450 ml of 0.1 M phosphate buffer amended with 600 μmol of spergon in a 1-liter Erlenmeyer flask. Treatments containing spergon or cells alone in phosphate buffer were also prepared. All flasks were incubated on a 180 rpm rotary shaker at 30° C. After 4 hours, the contents of each flask were centrifuged at 8,000×g for 10 mins. Portions of the supernatant fluid of each treatment were tested for the presence of chloride ions as described earlier. When it was found that the suspension consisting of spergon and *R. phaseoli* 203CR gave a positive qualitative test for chloride, a quantitative colorimetric test for chloride ions was performed with portions of the supernatant fluid of each treatment; for this purpose, the method of Bergmann and Sanik, *Analyst* (London) 29:241–245, (1957), was employed. The remainder of the supernatant liquid as well as all the cell pellets were acidified, and then extracted with ether followed by hexane extractions as described in the studies of phygon metabolism. The extracts were concentrated in a rotary flash evaporator and stored at 4° C. TLC analysis of spergon degradation products was performed as described in the studies of phygon metabolism except that in this case the chromatogram was developed with a solvent mixture of toluene-benzene-ethyl acetate-acetic acid (5:4:4:1).

Metabolism of Thiram. A washed cell suspension of thiram-tolerant *R. meliloti* 87TR (which was grown for 48 hours in 0.5% mannitol-mineral salts broth) was obtained as described above for cowpea Rhizobium. This cell suspension (with an optical density of 5.1 at 550 nm) was introduced into a 500 ml Erlenmeyer flask containing 200 ml of 0.1 M phosphate buffer (pH 7.0) which has been treated with 250 ppm thiram. A control flask containing 250 ppm thiram was not inoculated. Each flask was placed on a stirring plate and subjected to continuous mechanical stirring of the medium throughout the experiment. After about 15 mins. clean, dry $N_2$ flowing at a rate of approximately 40 ml/min., was passed in series through the medium into three different 30-ml, fritted glass, midget bubblers. The first contained 10.0 ml of a 2.0% aqueous solution of zinc acetate to remove any $H_2S$ produced (which might interfere with $CS_2$ absorption). The second contained 10.0 ml of Dickinson-Viles reagent to absorb any $CS_2$ evolved (Weed et al, *Contra, Boyce Thompson Inst.*, 17:299–315, 1953), and the third contained Pribyl-Nedbalkova solution for absorption of volatile dimethylamine (Pribyl and Nedbalkova, *Anal. Chem.*, 232:261–267, 1967). The experiment ran for two hours. The results given in the first column of Table 10 shows the *R. meliloti* 87TR converted thiram to dimethylamine and $CS_2$. Most of the thiram was converted to dimethylamine and $CS_2$, hence residual DMDT was negligible. The absorbed $CS_2$ was determined colorimetrically according to the method of Lindahl, *Lantbrukshogsk. Ann.*, 30:375–404 (1964). The nonvolatile water-soluble dimethylamine formed in the flask were extracted three times by shaking the 200 ml phosphate buffer medium with 67.0 of ether in a 500 ml separatory funnel. Dimethylamine was determined colorimetrically using the procedure of Pribyl and Nedbalkova, *Anal. Chem.*, 232:261–267 (1967). Similarly, residual thiram was extracted three times from the flask, using 67.0 ml of chloroform each time. The thiram content of the chloroform extract was determined colorimetrically (Keppel, *J. Assoc. Off. Agric. Chem.*, 39:708–712, 1956).

In a separate similar experiment, 250 ppm thiram was incubated with the thiram-tolerant Rhizobium in 200 ml of citrate buffer (0.25% aqueous solution), pH 8.1, in a 500 ml Erlenmeyer flask, and the medium wa stirred for about 1 hour without using $N_2$ to drive out the volatile gases. The amount of dimethyldithiocarbamate (DMDT) formed in the reaction medium was determined colorimetrically after adding 2.0 ml of 0.3% aqueous $CuSO_4.5H_2O$ per 10.0 ml of test solution, to develop the yellow-brown color (Lindah, supra). The result is shown in the second column of Table 10. Only 80% of the 250 ppm of the fungicide was recovered as DMDT. The partial recovery may have been partly because this product is unstable and also because some of the DMDT was retained with the thick suspension of the bacterial cells during extraction. The possible evolution of $H_2S$ and $SO_2$ during thiram decomposition was investigated by assaying for these gases using the methods of Adams et al, *Health Lab. Sci.*, 7:4–12; 157–163 (1970).

The identity of dimethyldithiocarbamate (DMDT), dimethylamine (DMA) and $CS_2$ were confirmed by various analytical procedures such as UV-absorption, gas chromatography and thin layer chromatography.

TABLE 10

Formation of dimethyldithiocarbamate, dimethylamine, and carbon disulfide from thiram by thiram-resistant *R. meliloti* 87TR

| Amount of thiram used, µg/ml | Conc. of products formed, µg/ml | | |
| --- | --- | --- | --- |
| | DMDT | DMA | $CS_2$ |
| 250* | — | 89.0 | 143 |
| 250 | 200.3 | — | — |

*There was no DMDT formed in the first column because most of the thiram was converted to DMA and $CS_2$, whereas in the second column, experiment was designed to determine DMDT only. Uninoculated flask contained 248.2 µg/ml of thiram at the end of the experiment Other known legume seed or soil fungicides known in the art include N-trichloromethylmercapto-4-cyclohexane-1,2-dicarboximide (Captan), ethylmercuricchloride (Ceresan), methyl mercury 8-hydroxyquinone, methylmercuric dicyandiamide (Panagen), N-methyldithiocarbamate, 1,2,3,4,5-pentachloronitrobenzene and dinitrotrichlorobenzene.

Other fungicides such as those described hereinabove can be used in the practice of this invention as can other Rhizobium strains. Likewise, the manipulative techniques and the materials of the examples can be modified or replaced in a manner within the skill of the art based on the above teachings.

The various Rhizobium strains employed or produced in the above examples have been deposited with the American Type Culture Collection, Rockville, Maryland, under the following accession numbers:

| | |
| --- | --- |
| *Rhizobium meliloti* 87 | ATCC 31234 |
| *Rhizobium meliloti* 87TR | ATCC 31235 |
| *Rhizobium phaseoli* 203 | ATCC 31236 |
| *Rhizobium phaseoli* 203CR | ATCC 31237 |
| Rhizobium cowpea K04SR | ATCC 31238 |
| Rhizobium cowpea K04SRPR | ATCC 31239. |

According to the provisions of the patent statutes there are described above the invention and what are now considered to be its best embodiments. However, within the scope of the appended claims, it is to be understood that the invention can be pracriced otherwise than specifically described.

What is claimed is:

1. A biologically pure culture of a fungicide resistant strain of Rhizobium, which strain has good infecting and nitrogen-fixing abilities in symbiosis with plants of the leguminosea family, prepared by a method which comprises:

cultivating, in the presence of a Rhizobium-medium and an amount of a selected fungicide sufficient to kill at least 90% of the Rhizobium culture initially present, a culture of Rhizobium bacteria of selected strain and inoculation group having good infecting and nitrogen-fixing ability, whereby bacteria strains sensitive to said amount of said fungicide are killed; subjecting the residual fungicide resistant bacteria to at least one additional cultivation step, as above, in the presence of an increased amount of said fungicide; and recovering a Rhizobium strain having increased resistance to said fungicide; said fungicide being selected from agriculturally useful legume seed or soil fungicides which adversely affect the Rhizobium bacteria being cultivated.

* * * * *